United States Patent
Smith et al.

[11] Patent Number: 6,124,343
[45] Date of Patent: Sep. 26, 2000

[54] SUBSTITUTED PHENYL COMPOUNDS WITH A SUBSTITUENT HAVING A THIENYL RING

[75] Inventors: Christopher Smith; Barry Porter; Roger Walsh; Tahir Majid; Clive McCarthy; Neil Harris; Peter Astles; Iain McLay; Andrew Morley; Andrew Bridge; Andrew Van Sickle; Frank Halley; Alan Roach; Martyn Foster, all of Dagenham, United Kingdom

[73] Assignee: Rhône-Poulenc Rorer Limited, West Malling, United Kingdom

[21] Appl. No.: 08/898,547

[22] Filed: Jul. 22, 1997

Related U.S. Application Data

[63] Continuation-in-part of application No. PCT/GB96/00120, Jan. 22, 1996.
[60] Provisional application No. 60/024,902, Aug. 30, 1996.

[30] Foreign Application Priority Data

| Jan. 27, 1919 | [GB] | United Kingdom | 9501635 |
| Mar. 1, 1995 | [GB] | United Kingdom | 9504061 |
| May 11, 1995 | [GB] | United Kingdom | 9509604 |
| Jul. 26, 1996 | [GB] | United Kingdom | 9615752 |

[51] Int. Cl.$^7$ .................... A61K 31/381; C07D 333/16
[52] U.S. Cl. .................. 514/438; 549/77; 549/78; 549/79
[58] Field of Search .................. 549/77, 78, 79; 514/438

[56] References Cited

U.S. PATENT DOCUMENTS

| 5,134,154 | 7/1992 | Freedman et al. . |
| 5,334,598 | 8/1994 | Bagley et al. . |
| 5,538,991 | 7/1996 | Ashton et al. . |

FOREIGN PATENT DOCUMENTS

| 0348155 | 12/1989 | European Pat. Off. . |
| 0617001 | 9/1994 | European Pat. Off. . |
| 0497740 | 12/1994 | European Pat. Off. . |
| 0569193 | 2/1997 | European Pat. Off. . |
| 63-135302 | 6/1988 | Japan . |
| 2277446 | 11/1994 | United Kingdom . |
| 94/21259 | 9/1994 | WIPO . |
| 95/03044 | 2/1995 | WIPO . |
| 95/13262 | 5/1995 | WIPO . |

*Primary Examiner*—Laura L. Stockton
*Attorney, Agent, or Firm*—Synnestvedt & Lechner LLP

[57] ABSTRACT

This invention is directed to compounds of formula I

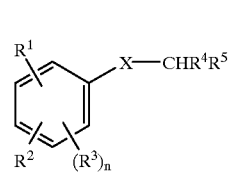

wherein $R^1$ is CN, $CH_2CN$, CH=CHCN, CHO, or CH=$CHCO_2H$;

$R^2$ is aryl lower alkoxy, heteroaryl lower alkoxy, aryl lower alkylthio or heteroaryl lower alkylthio wherein each of the aryl and heteroaryl moieties is optionally substituted;

$R^3$ is halogen;

$R^4$ is optionally substituted aryl or optionally substituted heteroaryl;

$R^5$ is carboxy or an acid isostere;

X is oxygen or sulphur; and n is zero or 1; or an N-oxide thereof, prodrug thereof solvate thereof, or pharmaceutically acceptable salt thereof, which compounds have endothelin antagonist activity. The invention is also directed to methods for preparing the compounds of formula I and their pharmaceutical use.

19 Claims, No Drawings

SUBSTITUTED PHENYL COMPOUNDS WITH A SUBSTITUENT HAVING A THIENYL RING

BACKGROUND OF THE INVENTION

This application is a continuation-in-part application of PCT International Application No. PCT/GB96/00120, filed internationally Jan. 22, 1996, designating the United States, and claims priority from United States Provisional Application No. 60/024,902, filed Aug. 30, 1996.

FIELD OF THE INVENTION

This invention is directed to substituted phenyl compounds, their preparation, pharmaceutical compositions containing these compounds, and their pharmaceutical use in the treatment of disease states associated with endothelin peptides.

Endothelins are a family of peptides, mainly synthesized and released by endothelial cells. The term endothelin (ET) refers to a family of homologous 21-amino acid peptides found in three distinct isoforms: ET-1, ET-2 and ET-3, and in the present specification the term "endothelin" is intended to refer to any or all of the isoforms of endothelin. Each endothelin isopeptide is encoded by a distinct gene with a distinct chromosomal locus for each human gene.

Receptor subtypes $ET_A$ and $ET_B$ specific for endothelin have been identified (H. Arai, et al., Nature, 348, 730 (1990) and T. Sakurai et al., Nature, 348, 732 (1990)). ET-1 and ET-2 bind more potently than ET-3 to $ET_A$, and stimulation of this receptor subtype promotes vasoconstriction. ET-1, ET-2 and ET-3 bind with equal affinity to $ET_B$ receptors, and stimulation of this receptor subtype can evoke vasodilatation or promote vasoconstriction.

Thus, endothelin is an important potent vasoconstrictor producing long-lasting effects in arteries and veins. Consequently, endothelin causes profound actions on the cardiovascular system in particular the coronary, renal, mesenteric and cerebral circulation. Other biological activities by endothelin are also observed.

Intravenous infusion of ET-1 to rats causes a transient hypotensive effect, followed by a sustained increase in blood pressure. Even low doses of endothelin, which alone are without pressor actions, potentiate the effects of other vasoconstrictor agents. Significantly elevated plasma immunoreactive ET-1 levels have been reported in patients with disorders such as myocardial infarction including acute myocardial infarction, coronary heart disease, unstable angina including vasospastic angina, preeclampsia, essential and pulmonary hypertension and congestive heart failure.

Renal blood vessels are particularly sensitive to the vasoconstrictor effect of ET. It produces a marked reduction in renal blood flow accompanied by reductions in glomerular filtration rate, urine volume and urinary sodium and potassium excretion. Endothelin is also mitogenic for mesangial cells. Thus, endothelin has a role in a number of renal disorders such as acute renal insufficiency and chronic renal insufficiency and cyclosporin induced nephrotoxicity. Furthermore, erythropoetin causes endothelin release and that release plays a role in renal complications and hypertension occurring as side effects in dialysis patients.

Endothelin induces a proliferative response in vascular smooth muscle cells and this, combined with observations of elevated circulating levels of ET-1 in atherosclerosis, indicates that endothelin contributes to the pathogenesis of this and related diseases. Levels of endothelin are also elevated after angioplasty and is implicated in the high level of restenosis after percutaneous transluminal angioplasty.

The cerebral vasculature is very sensitive to the pressor actions of the endothelins. A single intrathecal injection of ET-1 in dogs leads to a prolonged constriction of the basilar artery. Hypoxia and ischaemia are potent stimuli for increased release of endothelin by endothelial cells, while the secretion of endogenous vasodilators such as $PGI_2$ and endothelial derived relaxant factor are reduced. Therefore, endothelin plays an important role in cerebral ischaemia such as stroke and subarachnoid haemorrhage.

In addition to endothelin being an important vasoactive mediator, it exhibits a range of biological functions related to cellular activation and mitogenesis. Endothelin is now considered a pleuripotent mediator of cellular function (Warner, T. D. et al., Biochemical Pharmacology, 1994, 48(4), 625–635). These functions have particular relevance to tissue fibrosis since this disease is essentially a disorder of cellular proliferation and activation. Endothelial activation is present in the histological staging of fibrosis and precedes the deposition of extracellular matrix in the tissue. In addition, elevated ET-1 levels are associated with a variety of disease syndromes associated with tissue fibrosis. Giard et al., Lancet, 1993, 341, 1550–1554, have demonstrated significantly elevated ET-1 levels in a range of cell types involved in alveolar fibrosis. Cambrey, A. D. et al., Am. J. Respir. Cell. Mol. Biol., 1994, 11, 439–445, have demonstrated increased ET-1 levels in patients with systemic sclerosis and shown that this contributes to fibroblast mitogenic activity. Housset, C. N. et al., J.Hepatology, 1995, 22(Suppl.2), p55–60, have demonstrated that ET-1 mediated hepatic lipocyte contraction is implicated as a major cause of collagen band disruption and thus loss of the normal hepatic lobular structure in liver fibrosis. Seino et al., Am. Rev. Resp. Dis., 1995, 151, 4, A63, have demonstrated anti-fibrotic effects of the $ET_A$ selective receptor antagonist BQ123 in the hamster bleomycin model.

Fibrotic diseases are characterised by the excessive and deranged deposition of extracellular matrix proteins, notably collagen, with the tissue interstitial space. A range of mediators have been implicated in the initiation and modulation of this process but, as yet, there is no definite idea as to pathogenesis. In many respects fibrosis resembles uncontrolled wound healing.

The clinical consequences of fibrosis vary according to severity and the organ affected. For example, in the lungs and liver, where the integrity of the interstitial space is essential for organ function, fibrosis is a significant cause of morbidity and mortality. In the case of idiopathic pulmonary fibrosis, around 50% of affected patients die of the disease within five years of first hospital presentation. At the other end of the spectrum, fibrosis of, for example, the skin can be a cause of morbidity but rarely mortality.

Disease syndromes associated with tissue fibrosis include: pulmonary fibrosis (idiopathic and non-idiopathic); bronchitis (particularly in terms of vascular and epithelial remodelling characteristic of this disease); pulmonary fibrosis secondary to lung transplantation; iatrogenic fibrosis (drug induced lesions and radiotherapy induced fibrosis); post-infection lung fibrosis; liver fibrosis; post-infection (e.g. hepatitis) hepatic fibrosis; post-cirrhosis hepatic fibrosis; renal fibrosis; renal sclerosis; myocardial fibrosis; and systemic rheumatological disease (particularly rheumatoid arthritis and systemic sclerosis).

Endothelin is a potent contractor of isolated airway tissue including human bronchus. In addition, endothelin has been shown to induce eicosanoid release, possess mitogenic properties for airway smooth muscle and has pronounced inflammatory actions. All of these actions confirm an important role for endothelin in pulmonary pathophysiology and in asthma and related conditions.

Endothelin levels are elevated during septic shock and other endotoxin induced conditions such as disseminated intravascular coagulation, migraine, gastrointestinal disorders such as ulceration and irritable bowel syndrome, Raynauds disease and haemangioendothelioma.

Normal bone remodelling involves the coupling of osteoclast and osteoblast functions, an imbalance of these events leading to pathophysiological bone loss. Both cell types produce endothelin and possess endothelin receptors. Antagonists of selected actions of endothelin would therefore be useful in the treatment of clinical conditions of bone loss, such as osteoporosis.

Endothelin-1 is produced in the human prostrate and endothelin receptors have been identified in this tissue. Since endothelin is a paracrine contractile and proliferative factor in the prostrate gland, a role is indicated for endothelin in benign prostatic hyperplasia.

Endothelin is produced by tumour cells and in light of its mitogenic properties endothelin receptor antagonists would be useful adjuncts in cancer chemotherapy.

The further actions of endothelin on neurotransmitter release are also observed, indicating a role in certain disorders of the central nervous system.

We have now found a novel group of compounds which act as endothelin antagonists and are therefore of use in therapy, more particularly for the treatment of a disease state associated with a physiologically detrimental excess of endothelin or a disease state associated with pathological conditions that are modulated by inhibiting endothelin. Thus, according to a first aspect of the present invention, we provide a compound of formula (I):

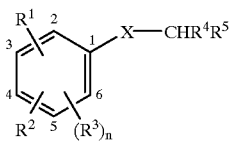

(I)

wherein
R$^1$ is CN, CH$_2$CN, CH=CHCN, CHO, or CH=CHCO$_2$H;
R$^2$ is aryl lower alkoxy, heteroaryl lower alkoxy, aryl lower alkylthio or heteroaryl lower alkylthio wherein each of the aryl and heteroaryl moieties is optionally substituted;
R$^3$ is halogen;
R$^4$ is optionally substituted aryl or optionally substituted heteroaryl;
R$^5$ is carboxy or an acid isostere;
X is oxygen or sulphur; and
n is zero or 1; and their N-oxides and prodrugs, and pharmaceutically acceptable salts thereof.

As used above, and throughout the description of the invention, the following terms in parentheses, unless otherwise indicated, shall be understood to have the following meanings:

"Acid isostere" means a group which is significantly ionised at physiological pH. Examples of suitable acid isosteres include sulpho, phosphono, alkylsulphonylcarbamoyl, tetrazolyl, arylsulphonylcarbamoyl, heteroarylsulphonylcarbamoyl or N-methoxycarbamoyl.

"Alkoxy" means an alkyl-O— group wherein the alkyl group is as described herein. Preferred alkoxy groups are lower alkoxy groups having 1 to about 3 carbon atoms. Exemplary alkoxy groups include methoxy, ethoxy and n-propoxy.

"Alkyl" means an aliphatic hydrocarbon group which may be straight or branched having about 1 to about 6 carbon atoms in the chain. Preferred alkyl groups have 1 to about 4 carbon atoms in the chain, especially 1 to about 2 carbon atoms. Branched means that one or more lower alkyl groups such as methyl, ethyl or propyl are attached to a linear alkyl chain. "Lower alkyl" means about 1 to about 4 carbon atoms in the chain which may be straight or branched. Exemplary alkyl groups include methyl, ethyl, n-propyl, i-propyl, n-butyl, t-butyl and n-pentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes alkyl, preferably lower alkyl, halogen for example chlorine, bromine or fluorine, CF$_3$, amino, nitro, cyano, alkoxy, preferably lower alkoxy and hydroxy, where alkoxy and alkyl are as defined herein.

"Aryl lower alkoxy" means aryl-lower alkyl-O— wherein the aryl and lower alkyl are as previously described.

"Aryl lower alkylthio" means aryl-lower alkyl-S— wherein the aryl and lower alkyl are as previously described.

"Halogen" means fluorine, chlorine, bromine or iodine.

"Heteroaryl" means about a 5- to about a 10-membered aromatic monocyclic or multicyclic hydrocarbon ring system wherein one or more of the carbon atoms in the ring system is/are element(s) other than carbon, for example nitrogen, oxygen or sulfur. The "heteroaryl" may also be substituted by one or more aryl group substituents. Exemplary heteroaryl groups include pyridazinyl, pyrazolyl, 1,3-benzodioxolyl, 1,3-benzoxazolyl, furanyl, thienyl, pyridyl, pyrimidinyl, isoxazolyl, thiazolyl, isothiazolyl, quinolinyl, indolyl, isoquinolinyl, oxazolyl and 1,2,4-oxadiazolyl. Preferred heteroaryl groups include (2-, 3- or 4-)pyridyl, 4-isothiazolyl, 1,3-benzodioxol-5-yl, pyridazin-4-yl and 3-thienyl.

"Heteroaryl lower alkoxy" means heteroaryl-lower alkyl-O— wherein the heteroaryl and lower alkyl are as previously described.

"Heteroaryl lower alkylthio" means heteroaryl-lower alkyl-S— wherein the heteroaryl and lower alkyl are as previously described.

"Patient" includes both human and other mammals.

"Pharmaceutically acceptable salt" means a salt form of the parent compound of formula I which is relatively innocuous to a patient when used in therapeutic doses so that the beneficial pharmaceutical properties of the parent compound of formula I are not vitiated by side-effects ascribable to a counter ion of that salt form. Pharmaceutically acceptable salt also includes a zwitterion or internal salt of the compound of formula (I).

"Prodrug" means a compound, for example an ester, which is convertible in vivo by metabolic means (e.g. by hydrolysis) to a compound of formula I.

The compounds of formula (I) and N-oxides and prodrugs thereof are useful in the form of the free base or acid or in the form of a pharmaceutically acceptable salt thereof. All forms are within the scope of the invention and references herein to a compound of the present invention includes a compound of formula (I) or an N-oxide or prodrug thereof together with a pharmaceutically acceptable salt of such a compound.

Where a compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on endothelin inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, such as hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isothionates and di-p-toluoyltartrates, methanesulfonate, ethanesulfonate, benzenesulfonate, p-toluenesulfonate, cyclohexylsulfamate and quinate, respectively.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on endothelin inherent in the free acid are not vitiated by side effects ascribable to the cations.

Pharmaceutically acceptable salts, including for example alkali and alkaline earth metal salts, within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

It will be apparent to those skilled in the art that certain compounds of formula (I) can exhibit isomerism, for example geometrical isomerism and optical isomerism. Geometrical isomers include the cis and trans forms of compounds of the invention having an alkenyl moiety. Optical isomers contain asymmetric centers. These asymmetric centers may independently be in either the R or S configuration. All isomers within formula (I), and their mixtures, are within the scope of the invention.

Such isomers can be separated from their mixtures, by the application or adaptation of known methods, for example chromatographic techniques such as chiral chromatography and resolution via chiral amine salts (e.g. a-methylbenzylamine or ephedrine salts), or they are separately prepared from the appropriate isomers of their intermediates, for example by the application or adaptation of methods described herein.

It is to be understood that the present invention is intended to cover all combinations of particular and preferred groupings as described herein.

It will be appreciated that within formula (I) above the groups $R^1$, $R^2$ and $R^3$ may be attached at any available position on the benzene ring. $R^1$ may preferably be attached ortho to the group —X—$CHR^4R^5$ (i.e. the ring 2-position). $R^3$ may preferably be attached at the ring 3-position. $R^2$ may preferably be attached at the ring 5-position (i.e. para to the preferred $R^1$ position).

Particular and preferred compounds within formula (I) include compounds wherein the individual moieties $R^1$ to $R^5$, X and n independently have the following meanings:

$R^1$ may particularly represent CN.

$R^2$ is preferably heteroaryl lower alkoxy, more preferably heteroarylmethoxy. Exemplary heteroarylmethoxy groups include pyridylmethoxy (e.g. 3-pyridylmethoxy or especially 4-pyridylmethoxy), pyridazinylmethoxy (e.g. pyridazin-4-ylmethoxy), thienylmethoxy (e.g. 3-thienylmethoxy), isothiazolylmethoxy (e.g. 4-isothiazolylmethoxy) and 1,3-benzodioxolylmethoxy (e.g. 1,3-benzodioxol-5-ylmethoxy).

When $R^3$ is present the halogen substituent may preferably be fluorine.

$R^4$ is preferably optionally substituted aryl; more preferably phenyl, or especially phenyl substituted at the ortho position relative to the attachment of the phenyl group to the rest of the molecule and optionally further substituted. Preferred phenyl group substituents include one or more (e.g. 1, 2 or 3) substituents selected from lower alkyl (e.g. methyl), halogen (e.g. chlorine or bromine), CN, lower alkoxy (e.g. methoxy) and $CF_3$.

$R^5$ may particularly represent carboxy.

X may particularly represent oxygen.

A particular group of compounds of the present invention are compounds of formula: (Ia)

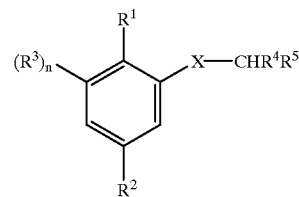

(Ia)

wherein $R^1$, $R^2$, $R^3$, $R^4$, $R^5$, n and X are as defined previously, and their N-oxides and prodrugs, and pharmaceutically acceptable salts thereof.

Compounds of formula (Ia) wherein $R^1$ represents CN are generally preferred.

Compounds of formula (Ia) wherein $R^2$ represents heteroaryl lower alkoxy, more particularly a heteroarylmethoxy group such as pyridylmethoxy (e.g. 3-pyridylmethoxy or especially 4-pyridylmethoxy), pyridazinylmethoxy (e.g. pyridazin-4-ylmethoxy), thienylmethoxy (e.g. 3-thienylmethoxy), isothiazolylmethoxy (e.g. 4-isothiazolylmethoxy) and 1,3-benzodioxolylmethoxy (e.g. 1,3-benzodioxol-5-ylmethoxy), are also preferred.

Compounds of formula (Ia) wherein —X—$CHR^4R^5$ represents —O—$CHR^4R^5$, more particularly where $R^4$ is optionally substituted aryl and $R^5$ is carboxy, are also preferred. Within —O—$CHR^4R^5$, $R^4$ is preferably phenyl substituted in the ortho position relative to the attachment of the phenyl group to the rest of the $R^4$ moiety by a lower alkyl (e.g. methyl), $CF_3$ or chlorine substituent and is optionally further substituted by one or more halogen, lower alkyl, CN or lower alkoxy groups.

A preferred group of compounds of the present invention are compounds of formula: (Ib)

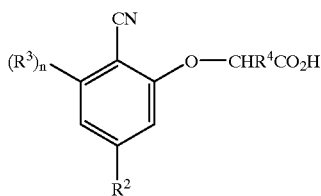

wherein $R^2$, $R^3$, $R^4$ and n are as defined previously, and their N-oxides and prodrugs, and pharmaceutically acceptable salts thereof.

Particularly preferred are compounds of formula (Ib) wherein $R^2$ is heteroarylmethoxy and $R^4$ is optionally substituted aryl (e.g. phenyl substituted in the ortho position by lower alkyl such as methyl, $CF_3$ or chlorine, and is optionally further substituted by one or more, e.g. 1, 2 or 3, substituents selected from halogen, lower alkyl, CN, and lower alkoxy).

Particular compounds of the invention are those wherein the chiral center associated with the carbon atom α to the moiety X within the group —X—$CHR^4R^5$, or the carbon atom α to the oxygen atom within the group —O—$CHR^4CO_2H$, has the (S) configuration.

Within (Ia) and (Ib), when present $R^3$ particularly represents a fluorine atom.

Compounds of formula (Ib) wherein $R^2$ is pyridylmethoxy (e.g. 3-pyridylmethoxy or especially 4-pyridylmethoxy), pyridazinylmethoxy (e.g. pyridazin-4-ylmethoxy), thienylmethoxy (e.g. 3-thienylmethoxy), isothiazolylmethoxy (e.g. 4-isothiazolylmethoxy) and 1,3-benzodioxolylmethoxy (e.g. 1,3-benzodioxol-5-ylmethoxy) are particularly preferred.

It will be appreciated that the terminology describing some of the isomers of compounds claimed herein, and prepared hereinafter, has been modified from that used in the UK priority applications GB9504061.4 and GB9509604.6 [where individually prepared enantiomers were differentiated as dextrorotatory (prefix +) according to the direction wherein, under specified conditions, they rotated the plane of polarised light], following an X-ray determination of the absolute stereochemistry associated with the chiral center of the carbon atom α to the oxygen atom within the group —O—CH(2-methylphenyl)$CO_2H$ of the Reference Example described as (S)-[5-(1,3-benzodioxol-5-ylmethoxy)-2-cyanophenoxy]-(2-methylphenyl)acetic acid, (−) ephedrine salt.

Particular compounds for use according to the invention are selected from the following:

(RS)-(2-chlorophenyl)-[2-cyano-5-(4-pyridylmethoxy)-phenoxy]acetic acid;
(RS)-[2-cyano-5-(3-thienylmethoxy)phenoxy]-phenylacetic acid;
(RS)-(2-chlorophenyl)-[2-cyano-5-(3-thienylmethoxy)-phenoxy]acetic acid;
(RS)-[5-(1,3-benzodioxol-5-ylmethoxy)-2-cyanophenoxy]-phenylacetic acid;
(RS)-[5-(1,3-benzodioxol-5-ylmethoxy)-2-cyanophenoxy]-(2-trifluoromethylphenyl)acetic acid;
(RS)-[2-cyano-5-(3-thienylmethoxy)phenoxy]-(2-methylphenyl)acetic acid;
(RS)-[5-(1,3-benzodioxol-5-ylmethoxy)-2-cyanophenoxy]-(2-chlorophenyl)acetic acid;
(RS)-(2-bromophenyl)-[2-cyano-5-(3-thienylmethoxy)-phenoxy]acetic acid;
(RS)-(3-chlorophenyl)-[2-cyano-5-(3-thienylmethoxy)-phenoxy]acetic acid;
(R)-(2-chlorophenyl)-[2-cyano-5-(3-thienylmethoxy)-phenoxy]acetic acid;
(S)-(2-chlorophenyl)-[2-cyano-5-(3-thienylmethoxy)-phenoxy]acetic acid;
(RS)-[2-cyano-5-(4-pyridylmethoxy)phenoxy]phenylacetic acid;
(RS)-[2-cyano-5-(3-thienylmethoxy)phenoxy]-(2-fluorophenyl)acetic acid;
(RS)-[2-cyano-5-(4-pyridylmethoxy)phenoxy]-(2-methylphenyl)acetic acid;
(RS)-[2-cyano-5-(3-thienylmethoxy)phenoxy]-(2-trifluoromethylphenyl)acetic acid;
(RS)-(2-bromophenyl)-[2-cyano-5-(4-pyridylmethoxy)-phenoxy]acetic acid;
(RS)-[2-cyano-5-(4-pyridylmethoxy)phenoxy]-(2-trifluoromethylphenyl)acetic acid;
(S)-[2-cyano-5-(4-pyridylmethoxy)phenoxy]-(2-methylphenyl)acetic acid;
(RS)-(2-chlorophenyl)-[2-cyano-5-(pyridazin-4-ylmethoxy)phenoxy]acetic acid;
(RS)-[5-(1,3-benzodioxol-5-ylmethoxy)-2-cyanophenoxy]-(2-methylphenyl)acetic acid;
(RS)-(2-chlorophenyl)-[2-cyano-5-(isothiazol-4-ylmethoxy)phenoxy]acetic acid;
(RS)-[2-cyano-5-(3-pyridylmethoxy)phenoxy]phenyl-acetic acid;
(RS)-[2-formyl-5-(3-thienylmethoxy)phenoxy]phenylacetic acid;
(RS)-N-{[2-cyano-5-(3-thienylmethoxy)phenoxy]-phenylacetyl}-4-isopropylbenzenesulphonamide;
(RS)-[2-cyano-5-(4-pyridylmethoxy)phenoxy]-(2-methylphenyl)acetic acid, acetoxy methyl ester;
(RS)-(2-chlorophenyl)-[2-cyano-3-fluoro-5-(3-thienylmethoxy)phenoxy]acetic acid;
(RS)-[5-(benzoxazol-6-ylmethoxy)-2-cyanophenoxy]-(2-chlorophenyl)acetic acid;
(RS)-[2-cyano-5-(4-pyridylmethoxy)phenoxy]-[2-(3-methyl)thienyl]acetic acid;
(RS)-[(2-cyano-5-(thiazol-5-ylmethoxy)phenoxy]-(2-methylphenyl)acetic acid;
(RS)-(2-chlorophenyl)-[2-cyano-3-fluoro-5-(4-pyridylmethoxy)phenoxy]acetic acid;
(RS)-2-[(2-chlorophenyl)-(1H-tetrazolyl-5-yl)methoxy]-4-(4-pyridylmethoxy)benzonitrile;
(RS)-[3-chloro-2-cyano-5-(4-pyridylmethoxy)phenoxy]-(2-chlorophenyl)acetic acid;

(RS)-[5-(benzoxazol-6-ylmethoxy)-2-cyanophenoxy]-(2-methylphenyl)acetic acid;
(S)-[5-(1,3-benzodioxol-5-ylmethoxy)-2-cyanophenoxy]-(2-methylphenyl)acetic acid;
(S)-[5-(1,3-benzodioxol-5-ylmethoxy)-2-cyano-3-fluorophenoxy]-(2-methylphenyl)acetic acid;
(RS)-[2-cyano-5-(4-(3-fluoropyridyl)methoxy)phenoxy]-(2-methylphenyl)acetic acid;
(RS)-2-[(2-methylphenyl)-(1H-tetrazol-5-yl)methoxy]-4-(4-pyridylmethoxy)benzonitrile;
(RS)-4-(1,3-benzodioxol-5-ylmethoxy)-2-[(2-methylphenyl)-(1H-tetrazol-5-yl)methoxy]benzonitrile;
(RS)-[2-cyano-3-fluoro-5-(4-pyridylmethoxy)phenoxy]-(2-methylphenyl)acetic acid;
(RS)-[5-(benzoxazol-6-ylmethoxy)-2-cyano-3-fluorophenoxy]-(2-methylphenyl)acetic acid;
(RS)-[5-(1,3-benzodioxol-5 -ylmethoxy)-2-cyano-3-fluorophenoxy]-(2-methylphenyl)acetic acid;
(RS)-[5-(benzoxazol-5-yl)methoxy-2-cyanophenoxy]-(2-methylphenyl)acetic acid;
(RS)-(5-benzyloxy-2-cyanophenoxy)-(2-methylphenyl)-acetic acid;
(RS)-[2-cyano-5-(furan-3-ylmethoxy)phenoxy]-(2-methylphenyl)acetic acid;
(RS)-N-methoxy-[2-cyano-5-(3-thienylmethoxy)phenoxy]-(2-methylphenyl)acetamide; and solvates (e.g. hydrates); and pharmaceutically acceptable salts thereof.

Particularly preferred compounds of the invention include:

(RS)-(2-chlorophenyl)-[2-cyano-5-(4-pyridylmethoxy)-phenoxy]acetic acid;
(S)-[5-(1,3-benzodioxol-5-ylmethoxy)-2-cyanophenoxy]-(2-methylphenyl)acetic acid;
(RS)-[5-(1,3-benzodioxol-5-ylmethoxy)-2-cyanophenoxy]-(2-methylphenyl)acetic acid;
(RS)-[2-cyano-5-(4-pyridylmethoxy)phenoxy]-(2-methylphenyl)acetic acid;
(S)-[2-cyano-5-(4-pyridylmethoxy)phenoxy]-(2-methylphenyl)acetic acid;
(RS)-[5-(1,3-benzodioxol-5-ylmethoxy)-2-cyano-3-fluorophenoxy]-(2-methylphenyl)acetic acid;
(S)-[5-(1,3-benzodioxol-5-ylmethoxy)-2-cyano-3-fluorophenoxy]-(2-methylphenyl)acetic acid; and solvates (e.g. hydrates); and pharmaceutically acceptable salts thereof.

An especially preferred compound of the invention is:

(S)-[5-(1,3-benzodioxol-5-ylmethoxy)-2-cyanophenoxy]-(2-methylphenyl)acetic acid; and solvates (e.g. hydrates); and pharmaceutically acceptable salts thereof.

Compounds of formula (I) and their N-oxides and pro-drugs and pharmaceutically acceptable salts thereof (hereinafter referred to as "compounds of the invention") exhibit pharmacological activity and accordingly are of use in therapy. More especially, they are endothelin inhibitors, in particular endothelin A inhibitors. Compounds of the invention accordingly are incorporated into pharmaceutical compositions and used in the treatment of patients suffering from certain medical disorders.

The present invention thus provides compounds of the invention and compositions containing compounds of the invention for use in the treatment of a patient suffering from, or subject to, conditions which can be ameliorated by the administration of an inhibitor of endothelin. For example, compounds within the present invention are useful for the treatment of diseases and conditions characterized by, or having an etiology involving pathogenic endothelin levels. Examples of disease states and conditions which can be ameliorated by the administration of inhibitors of endothelin such as compounds of the invention include vascular ischaemia, for example cerebrovascular disease including cerebral ischaemia such as stroke and subarachnoid haemorrhage, coronary disorders such as myocardial infarction including acute myocardial infarction, coronary heart disease, angina including unstable and vasospastic angina, preeclampsia, essential and pulmonary hypertension and congestive heart failure, renal disorders such as acute renal insufficiency and chronic renal insufficiency, cyclosporin induced nephrotoxicity, erythropoetin induced renal complications and hypertension, gastrointestinal disorders such as ulceration and irritable bowel syndrome, Crohn's disease, poor peripheral skeletal muscle disorders such as peripheral vascular disease, intermittent claudication and critical limb ischaemia, glaucoma, atherosclerosis and related diseases, hypertension, asthma, fibrosis, particularly tissue fibrosis including pulmonary fibrosis (idiopathic and non-idiopathic), bronchitis (particularly in terms of vascular and epithelial remodelling characteristic of this disease), pulmonary fibrosis secondary to lung transplantation, iatrogenic fibrosis (drug induced lesions and radiotherapy induced fibrosis), post-infection lung fibrosis, liver fibrosis, post-infection (e.g. hepatitis) hepatic fibrosis, post-cirrhosis hepatic fibrosis, renal fibrosis, renal sclerosis, myocardial fibrosis and systemic rheumatological disease (particularly rheumatoid arthritis and systemic sclerosis), chronic obstructive pulmonary disease, migraine, endotoxin and hemorrhagic shock, Raynauds disease, benign prostatic hyperplasia, metastatic prostate cancer, bone loss such as osteoporosis, restenosis after angioplasty, diabetic neuropathies and for the treatment of organ hypofunction, particularly hypofunction caused by surgery on or transplant of organs such as the liver. Compounds of the present invention are also useful as a therapy for promoting wound healing and as adjuncts in the treatment of cancer.

According to a further feature of the invention there is provided a method for the treatment of a human or animal patient suffering from, or subject to, conditions which can be ameliorated by the administration of an inhibitor of endothelin, especially $ET_A$, for example conditions as hereinbefore described, which comprises the administration to the patient of an effective amount of compound of the invention or a composition containing a compound of the invention "Effective amount" is meant to describe an amount of compound of the present invention effective in inhibiting endothelin and thus producing the desired therapeutic effect.

The present invention also includes within its scope pharmaceutical formulations which comprise at least one of the compounds of the invention in association with a pharmaceutically acceptable carrier or coating.

In practice compounds of the present invention may generally be administered parenterally, rectally or orally. The compounds of the invention may also be administered topically to treat peripheral vascular diseases.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, capsules, pills, granules, powders, aqueous solutions or suspensions, injectable solutions, elixirs, creams, ointments or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions, or solutions, are used they can contain emulsifying agents or agents which facilitate suspension, or solubilization. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions for inhalation containing a compound of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention Compositions for topical administration include creams and ointments formulated in accordance with known methods, such as a topical carrier such as Plastibase® (mineral oil gelled with polyethylene) and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg, preferably about 0.02 to about 50 mg/kg, and more preferably about 0.1 to about 25 mg/kg body weight (or from about 1 to about 5000 mg, preferably from about 5 to about 2000 mg) in single of 2 to 4 divided daily doses. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention can also be administered in combination with endothelin converting enzyme inhibitors, angiotensin II receptor antagonists, renin inhibitors, angiotensin converting enzyme inhibitors, α- and β-adrenoceptor agonists and antagonists, diuretics, potassium channel activators, calcium channel antagonists, nitrates, antiarrhythmic agents, positive inotropic agents, serotonin receptor agonists and antagonists, platelet activating factor antagonists, histamine receptor antagonists, proton pump inhibitors, antithrombotic and thrombolytic agents, lipid lowering agents, antibiotic agents and phosphodiesterase inhibitors. If formulated as a fixed dose, such combination products employ the compounds of the present invention within the dosage range described below and the other pharmaceutically active agent within its approved dosage range. The compounds of the present invention may also be formulated with or useful in conjunction with antifungal and immunosuppressive agents such as amphotericin B, cyclosporins and the like to counteract the hypertension and nephrotoxicity secondary to such compounds. The compounds of the present invention may also be used in conjunction with haemodialysis.

Compounds within the scope of the present invention exhibit marked pharmacological activities according to tests described in the literature and reported in detail in the Examples Section herein, which tests results are believed to correlate to pharmacological activity in humans and other mammals.

Thus, according to a further embodiment, we provide a compound of the invention for use in the treatment of a human or animal patient suffering from, or subject to, conditions which can be ameliorated by the administration of an inhibitor of endothelin, especially $ET_A$.

In another embodiment we provide the use of a compound of the invention in the manufacture of a medicament for the treatment of a human or animal patient suffering from, or subject to, conditions which can be ameliorated by the administration of an inhibitor of endothelin, especially $ET_A$.

Compounds of formula (I) may be prepared by the application or adaptation of known methods, which means methods used heretofore or described in the literature. In the following procedures $R^1$ to $R^5$, X and n are as defined in formula (I) unless otherwise stated.

Thus, according to a first process (A), a compound of formula (I) may be prepared by reacting a compound of formula (II):

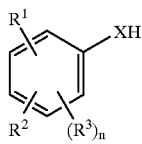

(II)

with a compound of formula (III):

Y—CHR⁴R⁵ᵃ    (III)

wherein Y is a leaving group such as a halogen atom or an aryl- or alkyl-sulphonyloxy group (e.g. methane- or p-toluene-sulphonyloxy) and $R^{5a}$ is a protected derivative of $R^5$, including carboxylic acid ammonium salts, followed by removal of the protecting group.

Compounds of formula (Ib) may thus be prepared by reacting a compound of formula: (IIa)

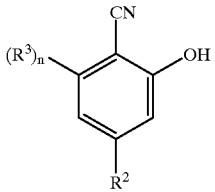

(IIa)

with a compound of formula (IIIa):

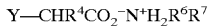

Y—CHR⁴CO₂⁻N⁺H₂R⁶R⁷    (IIIa)

wherein the cation is derived from a classical chiral base (e.g. ephedrine). Particular compounds of formula (Ib) wherein the chiral center associated with the O—CHR⁴CO₂H group has the (S)-configuration are prepared by reacting a compound of formula (IIa) with a compound of formula (IIIa) wherein the cation N⁺H₂R⁶R⁷ is derived from (−)-ephedrine.

The displacement reaction takes place in the presence of a suitable base such as an alkali metal carbonate (e.g. potassium carbonate, cesium carbonate), an alkali metal alkoxide (e.g. potassium t-butoxide), an alkali metal phosphate (e.g. potassium phosphate) which is a particularly suitable base for the reaction of (IIa) with (IIIa), or an alkali metal hydride (e.g. sodium hydride), followed where necessary by removing any protecting groups present. The reaction preferably takes place in an inert solvent such as an ether (e.g. tetrahydrofuran) optionally mixed with a ketone (e.g. tertiary butyl methyl ketone), a ketone (e.g. acetone or methyl ethyl ketone), or a dipolar aprotic solvent (e.g. dimethylformamide). The reaction conveniently takes place at a temperature of from about 10° C. to reflux.

When $R^{5a}$ is an alkoxycarbonyl group such as methoxycarbonyl conversion to a carboxyl group may be effected by hydrolysis using a base such as an alkali metal hydroxide or carbonate (e.g. sodium hydroxide, lithium hydroxide, potassium hydroxide or potassium carbonate) in the presence of an organic solvent such as an ether (e.g. dioxan or tetrahydrofuran) conveniently mixed with water. The reaction may be effected at a temperature in the range of from about ambient to reflux. Alternatively, acid hydrolysis may be used, for example using an inorganic acid such as hydrochloric acid in an organic solvent such as an ether (e.g. dioxan or tetrahydrofuran) conveniently mixed with water. The reaction may conveniently be effected at a temperature in the range of about ambient to about 80° C. When $R^{5a}$ is a t-butoxycarbonyl group the hydrolysis may conveniently be effected using trifluoroacetic acid at about ambient temperature.

According to another process (B), a compound of formula (I), wherein $R^1$ is CN attached at the ring 2-position, may be prepared by reacting a compound of formula (IV):

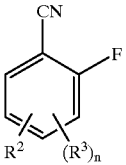

(IV)

with a compound of formula (V):

HOCHR⁴R⁵    (V)

or a corresponding thiol. A compound of formula (V) is initially treated with a suitable base such as sodium hydride to form an alkali metal salt which is reacted with (IV), preferably in an inert solvent such as dimethyl sulphoxide and conveniently at a temperature within the range of about room temperature and about 100° C. The thiol derivative may conveniently be treated with a suitable base such as an alkali metal alkoxide (e.g. sodium methoxide or potassium t-butoxide) and reacted with (IV) in the presence of a suitable solvent (e.g. an alcohol such as methanol or an ether such as tetrahydrofuran) at a temperature of from about ambient to reflux.

Another process (C) for preparing a compound of formula (I) wherein X is oxygen and $R^2$ is aryl lower alkoxy or heteroaryl lower alkoxy comprises treating a compound of formula (VI):

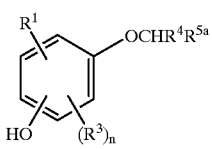

(VI)

wherein $R^{5a}$ is as defined previously, with an arylalkyl or heteroarylalkyl halide in the presence of a suitable base such as an alkali metal carbonate (e.g. potassium carbonate) or an alkali metal hydride (e.g. sodium hydride), followed where necessary by removing any protecting groups present. The displacement reaction preferably takes place in an inert solvent such as a ketone (e.g. acetone or methyl ethyl ketone) or a dipolar aprotic solvent such as dimethylformamide, conveniently at a temperature from about room temperature to reflux. Alternatively, a compound of formula (VI) may be treated with an arylalkyl or heteroarylalkyl alcohol in the presence of a triarylphosphine, such as triphenylphosphine, and a dialkyl ester, such as the diisopropyl or diethyl ester of azodicarboxylic acid, followed where necessary by removing any protecting groups present. The reaction preferably takes place in an inert solvent such as tetrahydrofuran, preferably at a temperature from about 0° C. to about room temperature.

Compounds of general formula (I) wherein $R^5$ is a carboxylic acid isostere may be prepared by the methodologies described herein, or conveniently from the corresponding acid. For example compounds of formula (I) wherein $R^5$ is alkylsulphonylcarbamoyl, arylsulphonylcarbamoyl or heteroarylsulphonylcarbamoyl, X is oxygen and $R^2$ is aryl lower alkoxy or heteroaryl lower alkoxy are prepared by treating a compound of formula (I) wherein $R^5$ is carboxy with an activating agent such as N,N'-carbonyldiimidazole in an inert solvent such as dichloromethane followed by reaction with the sodium salt of an alkylsulphonamide, arylsulphonamide or heteroarylsulphonamide and removal of any protecting groups present. The reaction preferably takes place in a dipolar aprotic solvent such as dimethylformamide at about room temperature.

"Prodrugs" of compounds of general formula (I), wherein $R^5$ is a carboxylic acid, such as carboxylic acid alkyl esters including acyloxyalkyl esters, may conveniently be prepared from the corresponding acid, for example by reaction with an appropriate alkyl halide, including acyloxyalkyl halides, in the presence of a suitable base such as an alkali metal carbonate (e.g. potassium carbonate) or an alkali metal hydride (e.g. sodium hydride). The reaction preferably takes place in a dipolar aprotic solvent such as dimethylformamide at about room temperature.

Intermediate compounds of formula (II), where $R^2$ represents aryl lower alkoxy or heteroaryl lower alkoxy and X represents an oxygen atom, may conveniently be prepared by treating a compound of formula (VII):

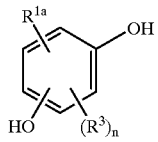

(VII)

where $R^{1a}$ is CHO, to introduce the groups $R^2$ and $R^1$ conveniently in that sequence.

The group $R^2$ may conveniently be introduced by reaction with an aryl or heteroaryl halide, or with an aryl or heteroarylmethanol according to the process (C) procedures.

When $R^1$ is CN this group may be introduced by conventional means, for example by treating the corresponding aldehyde with hydroxylamine or a salt thereof (e.g. the hydrochloride salt) to provide an oxime which may then be dehydrated, for example using acetic anhydride. Alternatively, the aldehyde may be reacted with a nitroalkane in acetic acid, preferably in the presence of sodium acetate or ammonium hydrogen phosphate, according to the procedure described in JACS 1961, 83, 2203. Alternatively, the aldehyde may be reacted with hydroxylamine-O-sulphonic acid preferably in an alcoholic solvent (e.g. aqueous ethanol) and conveniently at a temperature about room temperature, followed by treatment with an alkali metal hydroxide such as sodium hydroxide.

When $R^1$ is $CH_2CN$ this group may be introduced by reducing the aldehyde to $CH_2OH$, followed by conventional conversion of the hydroxy group to a suitable leaving group such as halo, alkylsulphonyloxy or arylsulphonyloxy, which is then converted to $CH_2CN$ by a conventional displacement reaction using an inorganic nitrile.

When $R^1$ is CH=CHCN or CH=CHCO$_2$H these groups may be introduced by a conventional Wittig or Horner-Emmons reaction on the corresponding aldehyde, followed by removal of any protecting groups where necessary.

It will be appreciated that the aforementioned conversions may also be applied to a compound wherein one or both of the formula (VII) hydroxyl groups is/are replaced by SH to provide a compound wherein X is sulphur and/or $R^2$ is aryl lower alkylthio or heteroaryl lower alkylthio.

Compounds of formula (III) where Y is a bromine atom may conveniently be prepared by reaction of the corresponding compound wherein Y is hydrogen with N-bromosuccinimide and azobisisobutyronitrile in an inert solvent such as chloroform at a temperature at about reflux.

Compounds of formula (III) where Y is a bromine atom may also be prepared by reaction of the corresponding compound wherein Y is hydroxyl with carbon tetrabromide and triphenylphosphine in an inert solvent such as dichloromethane at a temperature at about ambient temperature.

Compounds of formula (III) where Y is a bromine or chlorine atom may also be prepared by reaction of the corresponding compound wherein Y is hydroxyl with thionyl bromide, or thionyl chloride in an inert solvent such as toluene at a temperature at about ambient temperature.

Compounds of formula (III) where Y is alkylsulphonyloxy such as methanesulphonyloxy or arylsulphonyloxy such as p-toluenesulphonyloxy may conveniently be prepared by reaction of the corresponding compound wherein Y is hydroxyl with an alkyl- or aryl-sulphonyl halide such as methane- or p-toluene-sulphonyl chloride in the presence of a base, such as pyridine. The reaction may be carried out in an inert solvent such as a halogenated hydrocarbon (e.g. dichloromethane) at a temperature from about ambient to reflux.

Compounds of formula (IIIa) where Y is a bromine atom and the cation $N^+H_2R^6R^7$ is derived from a classical chiral base (e.g. (−)-ephedrine), may be prepared by reaction of compounds of formula (III), where Y is a bromine atom and $R^{5a}$ represents carboxy, with a suitable chiral base (e.g. (−)-ephedrine), in the presence of a racemization enhancing agent (e.g. tetra-n-butylammonium bromide). The reaction is carried out in an inert solvent such as ethyl acetate at a temperature at about ambient temperature.

Compounds of formula (IV) wherein $R^2$ is aryl lower alkoxy or heteroaryl lower alkoxy may conveniently be prepared from corresponding compounds wherein $R^2$ is hydroxyl according to the procedure described in process (C) above. The phenol precursors are either known compounds described, for example, by S. M. Kelly, Helv. Chim. Acta 1984, volume 67, p1572–1579 or may be prepared by similar methods to those described therein. The corresponding thiols may also be used to prepare compounds of formula (IV) wherein $R^2$ is aryl lower alkylthio or heteroaryl lower alkylthio.

Compounds of formula (VI), may conveniently be prepared from compounds of formula (VII), wherein $R^{1a}$ represents CHO, by first treating said compound of formula (VII), with an allyl halide (e.g. allyl bromide) in the presence of a suitable base such as a carbonate (e.g. potassium carbonate) to give a compound of formula (VIII):

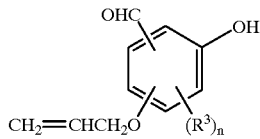

(VIII)

The reaction is facilitated by the addition of potassium iodide and tetrabutylammonium bromide. The reaction preferably takes place in an inert solvent such as a ketone (e.g. acetone or methyl ethyl ketone) at a temperature from about room temperature to reflux. Alternatively the reaction may be carried out in the presence of an alkali metal hydride such as sodium hydride in a dipolar aprotic solvent such as dimethylformamide at a temperature from about room temperature to about 100° C.

The group CHO in a compound of formula (VIII) may then be converted to the desired R¹ group using the procedures described above. Said compound may then be converted to a compound of formula (IX):

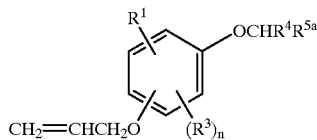

(IX)

by treatment with a compound of formula (III) according to the procedure in process (A) above. Finally, a compound of formula (IX) may be converted to a compound of formula (VI) by reaction with 1,4-diazabicyclo[2.2.2]octane and tris(triphenylphosphine)rhodium(I) chloride, preferably in an alcoholic solvent (e.g. aqueous ethanol) and conveniently at a temperature from about room temperature to reflux.

Intermediates of formula (V), thiol derivatives thereof and those of formula (III) wherein Y is hydrogen or hydroxyl are either known compounds described, for example, in J. Med. Chem., 17, 34 (1974), Org. Synth. Coll. Vol. I, page 336, Ark. Kemi, 24B(15), 1947, EP-A-0617001 and Tetrahedron Letters, 36, 1759, (1995) or may be prepared by using methods analogous to those described therein.

Intermediates of formula (V) may also be prepared from the corresponding keto-esters by reduction with sodium borohydride in an inert solvent such as tetrahydrofuran at a temperature at or about 0° C., followed by hydrolysis using a base such as an alkali metal hydroxide (e.g. sodium hydroxide) in the presence of an organic solvent such as an ether (e.g. dioxan) conveniently mixed with water. The reaction may be effected at a temperature from about ambient to reflux.

Compounds of formula (VII) are known compounds which are readily available from commercial sources. The corresponding mercaptans are either known in the art or may be prepared from compounds of formula (VII) using routine procedures.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, wherein case the salt separates directly or can be obtained by concentration of the solution.

The parent compounds of this invention can be regenerated from the acid addition salts by the application or adaptation of known methods. For example, parent compounds of the invention can be regenerated from their acid addition salts by treatment with an alkali, such as aqueous sodium bicarbonate solution or aqueous ammonia solution.

(S)-[5-(1,3-benzodioxol-5-ylmethoxy)-2-cyanophenoxy]-(2-methylphenyl)acetic acid may conveniently be prepared by treating (S)-[5-(1,3-benzodioxol-5-ylmethoxy)-2-cyanophenoxy]-(2-methylphenyl)acetic acid, (−) ephedrine salt with a mineral acid, such as hydrochloric acid or sulphuric acid. The reaction may conveniently be effected at a temperature at about ambient temperature and in an inert solvent, such as ethyl acetate.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Sodium (S)-[5-(1,3-benzodioxol-5-ylmethoxy)-2-cyanophenoxy]-(2-methylphenyl)acetate may conveniently be prepared by treating (S)-[5-(1,3-benzodioxol-5-ylmethoxy)-2-cyanophenoxy]-(2-methylphenyl)acetic acid (I) with sodium hydroxide. The reaction may conveniently be effected in an alcohol, such as ethanol at a temperature at about room temperature.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

As will be self-evident to those skilled in the art, some of the compounds of this invention do not form stable acid addition salts. However, acid addition salts are most likely to be formed by compounds of this invention having a nitrogen-containing heteroaryl group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be appreciated that it may be necessary to protect any labile groups such as hydroxyl groups when performing certain of the reactions described above. Conventional protection and subsequent deprotection procedures may be employed. Thus, for example, a hydroxyl group may conveniently be protected as an acyloxy group (e.g. acetoxy); the hydroxyl group may be regenerated by base-catalysed hydrolysis. Other conventional hydroxyl protecting groups may also be employed, for example as described by in Protective Groups in Organic Synthesis by Theodora W. Greene (John Wiley & Sons Inc. 1991).

The following Examples illustrate the preparation of the compounds according to the invention and the Reference Examples illustrate the preparation of the intermediates. It is to be understood that the Examples are purely illustrative, and are not intended to limit the invention in any way.

In the nuclear magnetic resonance (NMR) spectra, chemical shifts are expressed in ppm relative to tetramethylsilane. Abbreviations have the following meanings:

s=singlet, d=doublet, t=triplet, q=quartet, m=multiplet, dd=doublet of doublets.

Chiral HLPC determination to establish the enantiomeric purity of individual isomers, as the free acids, was carried out using a Chiralpak AD column (Diacel) and a mobile phase of heptane/isopropanol/trifluoroacetic acid (400/100/1, by volume), with UV detection at 254 nM.

EXAMPLE 1

(RS)-(2-Chlorophenyl)-[2-cyano-5-(4-pyridylmethoxy)phenoxy]acetic Acid

A solution of Reference Example 7 (0.35 g) in dioxan (25 ml) was treated with 1 N sodium hydroxide (5 ml) and stirred at ambient temperature for 6 hours. Water (50 ml) was added and the solution acidified to pH 2 with 2 N hydrochloric acid. The mixture was extracted three times with ethyl acetate (25 ml) and the combined extracts were washed with brine (25 ml), dried over magnesium sulphate and evaporated. The residue was dissolved in 1 N sodium hydroxide (10 ml) and the solution acidified to pH 2 by addition of concentrated hydrochloric acid. The resulting solid was filtered and washed with water to give a pale yellow solid, which was recrystallized from isopropanol to provide the title compound (100 mg), m.p. 225–226° C. [Elemental analysis:-C,63.98; H,3.80; N,7.07%. Calculated:-C,63.88; H,3.83; N,7.10%].

EXAMPLE 2

(RS)-[2-Cyano-5-(3-thienylmethoxy)phenoxy]-phenylacetic Acid

A solution of Reference Example 8 (600 mg) in dioxan (17 ml) was treated with 1 N sodium hydroxide (4.74 ml) and stirred at room temperature for 1 hour. The solution was brought to pH 7 by addition of 2 N hydrochloric acid and evaporated to remove dioxan. The residue was diluted with water and the solution adjusted to pH 1. The mixture was extracted with ethyl acetate, washed with water, dried and evaporated. The residue was triturated with pentane to give the title compound as a yellow solid (440 mg). [Elemental analysis:-C,65.7; H,4.40; N,3.69%. Calculated:-C,65.7; H,4.14; N,3.83%]. $^1$H NMR (CDCl$_3$): 5.0 (2H,s), 5.65 (1H,s), 6.5 (1H,s), 6.6 (1H,d), 7.05 (1H,d), 7.2–7.4 (5H,m), 7.45 (1H,d), 7.6 (2H,d).

EXAMPLE 3

(RS)-(2-Chlorophenyl)-[2-cyano-5-(3-thienylmethoxy)phenoxy]acetic Acid

A solution of Reference Example 11 (1.5 g) in dioxan (20 ml) was treated with 1 N sodium hydroxide (13 ml) and stirred at ambient temperature for 1 hour. Water (30 ml) was added and the solution acidified to pH 1 by addition of 2 N hydrochloric acid. The mixture was extracted four times with ethyl acetate (100 ml). The combined extracts were washed four times with water (50 ml), four times with brine (50 ml), dried over magnesium sulphate and evaporated. Pentane (50 ml) was added to the residual oil followed by evaporation giving a cream coloured solid which was dissolved in ether (20 ml) and reprecipitated by addition of pentane (20 ml) to give the title compound (1.5 g) as a cream coloured solid, m.p. 68–70° C. [Elemental analysis:-C, 60.29; H,4.47; N,3.26%. Calculated for $C_{20}H_{14}ClNO_4S.0.5Et_2O$:-C,60.07; H,3.52; N,3.50%].

EXAMPLE 4

(RS)-[5-(1,3-Benzodioxol-5-ylmethoxy)-2-cyanophenoxy]-phenylacetic Acid

A solution of Reference Example 16 (0.75 g) in dioxan (10 ml) was treated with 1 N sodium hydroxide (5.4 ml) and stirred at ambient temperature for 1.5 hours. Water (10 ml) was added and the solution acidified to pH 2 by addition of 2 N hydrochloric acid. The mixture was extracted three times with ethyl acetate (25 ml). The combined extracts were washed with brine (25 ml), dried over magnesium sulphate and evaporated. The residual yellow oil was purified by flash chromatography on silica eluting with a mixture of ethyl acetate and light petroleum (bp 40–60° C.) (1:1, v/v). Fractions containing the required product were combined and evaporated. This material was further purified by flash chromatography on silica eluting initially with a mixture of light petroleum (bp 40–60° C.) and ethyl acetate (5:1, v/v) then with a mixture of light petroleum (bp 40–60° C.) and ethyl acetate (10:3, v/v). Fractions homogenous in the required product were combined and evaporated to give the title compound (1.5 g) as a cream coloured solid, m.p. 68–70° C. [Elemental analysis:-C,66.36; H,4.95; N,2.85%. Calculated for $C_{23}H_{17}NO_6.0.6H_2O$:-C,66.63; H,4.44; N,3.38%].

EXAMPLE 5

(RS)-[5-(1,3-Benzodioxol-5-ylmethoxy)-2-cyanophenoxy]-(2-trifluoromethylphenyl)acetic Acid A solution of Reference Example 19 (0.35 g) in dioxan (5 ml) was treated with 1 N sodium hydroxide (2.16 ml) and stirred at ambient temperature for 2 hours. Water (10 ml) was added and the solution acidified to pH 1 with 2 N hydrochloric acid. The mixture was extracted three times with ethyl acetate (20 ml) and the combined extracts were washed with brine (20 ml), dried over magnesium sulphate and evaporated. The residual yellow oil was purified by flash chromatography on silica eluting with a mixture of dichloromethane and methanol (95:5, v/v). Fractions homogenous in the required product were combined and evaporated. The residue was triturated with a mixture of diisopropyl ether and pentane to give the title compound (0.25 g) as a white solid, m.p. 137–138° C. [Elemental analysis:-C,61.08; H,3.48; N,3.11%. Calculated:-C,61.15, H,3.42; N,2.97%].

EXAMPLE 6

(RS)-[2-Cyano-5-(3-thienylmethoxy)phenoxy]-(2-methylphenyl)acetic Acid

A solution of Reference Example 22 (0.55 g) in dioxan (10 ml) was treated with 1 N sodium hydroxide (4.5 ml) and stirred at ambient temperature for 2 hours. Water (10 ml) was added and the solution acidified to pH 1 with 2 N hydrochloric acid. The mixture was extracted four times with ethyl acetate (100 ml). The combined extracts were washed twice with water (10 ml), twice with brine (10 ml), dried over magnesium sulphate and evaporated. The residual pink solid was triturated with pentane (20 ml). The solid was dissolved in ethyl acetate and the solution filtered through a pad of silica. Evaporation of the filtrate and trituration of the resulting solid with ether (10 ml) gave the title compound (0.28 g) as a colourless solid, m.p. 146–148° C. [Elemental analysis:-C,66.80; H,4.49; N,3.69; S,8.45%. Calculated:-C, 66.50; H,4.52; N,3.69; S,8.47%].

EXAMPLE 7

(RS)-[5-(1,3-Benzodioxol-5-ylmethoxy)-2-cyanophenoxy]-(2-chlorophenyl)acetic Acid A solution of Reference Example 23 (0.35 g) in dioxan (5 ml) was treated with 1 N sodium hydroxide (2 ml) and stirred at ambient temperature for 1 hour. Water (10 ml) was added and the solution acidified to pH 1 with 2 N hydrochloric acid. The mixture was extracted three times with ethyl acetate (20 ml). The combined extracts were washed with brine (20 ml), dried over magnesium sulphate and evaporated. The residual yellow oil was purified by flash chromatography on silica eluting with a mixture of ethyl acetate and methanol (4:1, v/v). Fractions homogenous in the required product were combined and evaporated. The residue was triturated with a mixture of diisopropyl ether and pentane to give the title compound (0.25 g) as a white solid, m.p. 144–145° C. [Elemental analysis:-C,61.08; H,3.48; N,3.11%. Calculated:-C,61.15; H,3.42; N,2.97%].

EXAMPLE 8

(RS)-(2-Bromophenyl)-[2-cyano-5-(3-thienylmethoxy)phenoxy]acetic Acid

A solution of Reference Example 28 (0.48 g) in dioxan (5 ml) was treated with 1 N sodium hydroxide (3.14 ml) and stirred at ambient temperature for 1.5 hours. Water (30 ml) was added and the solution acidified to pH 2 with 2 N hydrochloric acid. The mixture was extracted three times with ethyl acetate (50 ml). The combined extracts were washed with water, dried over magnesium sulphate and evaporated. The residual light brown semi-solid was triturated with pentane to give the title compound (0.39 g) as a white solid, m.p. 89–98° C.

EXAMPLE 9

(RS)-(3-Chlorophenyl)-[2-cyano-5-(3-thienylmethoxy)phenoxy]acetic Acid

A solution of Reference Example 31 (1 g) in dioxan (20 ml) was treated with 1 N sodium hydroxide (9 ml) and stirred at ambient temperature for 1 hour. Water (10 ml) was added, the mixture filtered and the filtrate acidified to pH 1 with 2 N hydrochloric acid. The mixture was extracted four times with ethyl acetate (50 ml). The combined extracts were washed with brine (50 ml), dried over magnesium sulphate and evaporated. Ether (10 ml) was added to the residual oil and the resulting cream coloured solid was purified by flash chromatography on silica eluting with ethyl acetate. Fractions homogenous in the required product were combined and evaporated. The residue was dissolved in ether (10 ml) and pentane (10 ml) was added to give the title compound (0.3 g) as a colourless solid, m.p. 134–136° C. [Elemental analysis:-C,60.72; H,4.62; N,2.98; S,7.08; Cl,7.91%. Calculated:-C,60.48; H,4.38; N,3.20; S,7.33; Cl,8.11%].

EXAMPLE 10

(R)-(2-Chlorophenyl)-[2-cyano-5-(3-thienylmethoxy)phenoxy]acetic Acid and (S)-(2-chlorophenyl-[2-cyano-5-(3-thienylmethoxy)phenoxy]acetic Acid The product of Example 3 was separated into its (R) and (S) enantiomers by chiral HPLC using the following conditions:-Chiracel OD column; mobile phase of isopropanol/trifluoroacetic acid/heptane (10:0.25:90, v/v); flow rate 1 ml/minute; temperature ambient; UV detection at 270 nm.

EXAMPLE 11

(RS)-[2-Cyano-5-(4-pyridylmethoxy)phenoxy]-phenylacetic Acid

A stirred solution of (RS)-mandelic acid (0.304 g) in dry dimethyl sulphoxide (10 ml) was treated with sodium hydride (0.16 g, 60% dispersion in mineral oil) at room temperature. After 15 minutes Reference Example 32 (0.457 g) was added and stirring was continued for 1.25 hours at ambient temperature, then at 50° C. for 30 minutes. Water (20 ml) was added and the solution acidified to pH 2.5 with 2 N hydrochloric acid. A small amount of sodium chloride was added and the mixture extracted three times with ethyl acetate (50 ml). The combined extracts were washed with brine, dried over magnesium sulphate and evaporated. The residue was triturated with pentane, the solid washed with ether and recrystallized from ethanol to give the title compound (0.08 g) as a pale yellow solid, m.p. 218–220° C. [Elemental analysis:-C,69.77; H,4.43; N,7.74%. Calculated:-C,69.99; H,4.48; N,7.78%].

EXAMPLE 12

(RS)-[2-Cyano-5-(3-thienylmethoxy)phenoxy]-(2-fluorophenyl)acetic Acid

A solution of Reference Example 33 (0.66 g) in dioxan (6 ml) was treated with 1 N sodium hydroxide (4.98 ml) and stirred at ambient temperature for 1.5 hours. Water (50 ml) was added and the solution acidified to pH 2 with 2 N hydrochloric acid. The mixture was extracted three times with ethyl acetate (30 ml). The combined extracts were washed twice with water (10 ml), dried over magnesium sulphate and evaporated. The residual green coloured oil (0.9 g) was triturated twice with pentane (30 ml) affording the title compound as a pale yellow solid, m.p. 159–161° C. [Elemental analysis:-C,62.4; H,3.89; N,3.49; S,7.95%. Calculated:-C,62.65; H,3.68; N,3.65; S,8.36%].

EXAMPLE 13

(RS)-[2-Cyano-5-(4-pyridylmethoxy)phenoxy]-(2-methylphenyl)acetic Acid

A stirred mixture of (RS)-α-hydroxy-(2-methylphenyl) acetic acid [7.0 g; I. I. Lipkin and A. V. Ljubimowa *Zh. Obschch. Khim* 1948, 18, 701 (C.A. 1949, 43, 188)] and Reference Example 32 (9.5 g) in dry dimethyl sulphoxide was treated portionwise with sodium hydride (4.0 g of 60% w/w dispersion in mineral oil, 100 mmol) over 1 hour. The reaction was stirred a further 3 hours at ambient temperature before being concentrated under reduced pressure. The residue was partitioned between water (500 ml) and three amounts of dichloromethane (200 ml). The aqueous layer was acidified to pH 2–3 with concentrated hydrochloric acid and extracted with ethyl acetate (1000 ml). The organic layer was dried over magnesium sulphate and heated on a steam bath until the total volume was reduced to 100 ml. On standing a white solid was deposited. Recrystallization from isopropanol gave the title compound (10.0 g) as a white solid, m.p. 198–201° C. [Elemental analysis:-C,70.42; H,4.79; N,7.56%. Calculated:-C,70.58; H,4.85; N,7.48%].

EXAMPLE 14

(RS)-[2-Cyano-5-(3-thienylmethoxy)phenoxy]-(2-trifluoromethylphenyl)acetic Acid

A solution of Reference Example 34 (0.8 g) in dioxan (40 ml) was treated with 1 N sodium hydroxide (5 ml) and stirred at ambient temperature for 1 hour. Water (40 ml) was added and the solution acidified to pH 1 with 2 N hydrochloric acid. The mixture was extracted four times with ethyl acetate (80 ml). The combined extracts were washed with water (10 ml) then brine (10 ml), dried over magnesium sulphate and evaporated. The residual gum was triturated with a mixture of diethyl ether (20 ml) and pentane (5 ml) and the resulting solid (0.38 g) was dissolved in ethyl acetate. This solution was filtered through a pad of silica.

Evaporation of the filtrate afforded the title compound (0.18 g) as a colourless solid, m.p. 38–40° C. [Elemental analysis:-C,58.55; H,3.66; N,2.98%. Calculated:-C,58.19; H,3.25; N,3.23%].

EXAMPLE 15

(RS)-(2-Bromophenyl)-[2-cyano-5-(4-pyridylmethoxy)phenoxy]acetic Acid

A stirred solution of (RS)-a-hydroxy-(2-bromophenyl) acetic acid (0.46 g) in dry dimethyl sulphoxide (15 ml) was treated with sodium hydride (0.16 g, 60% dispersion in mineral oil) at room temperature. After 1 hour Reference Example 32 (0.46 g) was added and stirring was continued for 24 hours at ambient temperature. Water (50 ml) was added and the pH of the solution adjusted to 3–4 with 2 N hydrochloric acid and the mixture extracted twice with ethyl acetate (75 ml). The combined extracts were dried over magnesium sulphate, evaporated and the residue purified by flash chromatography on silica eluting initially with ethyl acetate then with a mixture of ethyl acetate and methanol (4:1, v/v). Fractions homogenous in the required product were combined and evaporated. The residual yellow oil was dissolved in 1 N sodium hydroxide (10 ml), the solution filtered and the filtrate acidified to pH 3. The resulting yellow solid (0.22 g) was washed well with water and recrystallized from isopropanol affording the title compound (0.1 g) as a pale yellow solid, m.p. 171–172° C. [Elemental analysis:-C,57.1; H,4.14; N,6.09%. Calculated:-C,57.42; H,3.44; N,6.38%].

EXAMPLE 16

(RS)-[2-Cyano-5-(4-pyridylmethoxy)phenoxy]-(2-trifluoromethylphenyl)acetic Acid, Monohydrochloride A stirred solution of (RS)-a-hydroxy-(2-trifluoromethylphenyl)acetic acid (1.1 g; R. Belcher et al., Analytica Chimica Acta, 1954, 10, 34) in dry dimethyl sulphoxide (40 ml), at room temperature, was treated portionwise with sodium hydride (0.4 g, 60% dispersion in mineral oil). After stirring for 0.75 hours at ambient temperature Reference Example 32 (1.14 g) was added and stirring was continued for 8 hours. The reaction mixture was stood at room temperature for 3 days then evaporated. The residue was partitioned between water and dichloromethane. The aqueous phase was acidified to pH 3 with concentrated hydrochloric acid and extracted three times with ethyl acetate. The combined extracts were dried over magnesium sulphate, evaporated and the residue triturated with diethyl ether to give a yellow solid. Recrystallization from isopropanol afforded the title compound (0.1 g) as a white solid, m.p. 200° C. (dec) [Elemental analysis:-C,57.22; H,3.24; N,6.10%. Calculated for $C_{22}H_{15}F_3N_2O_4.HCl$:-C,56.84; H,3.46; N,6.03%].

EXAMPLE 17

(S)-[2-Cyano-5-(4-pyridylmethoxy)phenoxy]-(2-methylphenyl)acetic Acid

A mixture of Example 13 (6.0 g) and (−)-ephedrine (3.0 g) was dissolved in ethanol (50 ml) and allowed to stand at ambient temperature for 18 hours. The resultant solid was collected and recrystallized from ethanol to leave a white solid (3.3 g). A sample of this solid (0.5 g) was stirred in water (50 ml) and treated with 1 N hydrochloric acid until the pH was 2–3. After stirring a further 15 minutes, the mixture was extracted twice with dichloromethane (50 ml). The combined extracts were dried over magnesium sulphate and evaporated. The residue was recrystallized from ethyl acetate to leave the title compound (0.2 g) as a white fluffy solid, m.p. 215° C. (dec); $[a]_D^{20}+125°$ (c=0.005, dimethyl sulphoxide). [Elemental analysis:-C,70.34; H,4.89; N,7.53%. Calculated:-C,70.58; H,4.85; N,7.48%].

EXAMPLE 18

(RS)-(2-Chlorophenyl)-[2-cyano-5-(pyridazin-4-ylmethoxy)phenoxy]acetic Acid

A solution of Reference Example 35 (0.2 g) in dioxan (6 ml) was treated with 1 N sodium hydroxide (1.47 ml) and stirred at ambient temperature for 1 hour. The reaction mixture was evaporated at 40° C., the residue diluted with water (6 ml) and the solution acidified to pH 3 with 2 N hydrochloric acid. The resulting solid was filtered, stirred with water (5 ml) for 1 hour, washed with ether (6 ml) and dried under vacuum at 40° C. affording the title compound (0.048 g) as an off-white amorphous solid, m.p. 203–205° C. [Elemental analysis:-C,60.9; H,3.71; N,10.3%. Calculated:-C,60.7; H,3.57; N,10.6%].

EXAMPLE 19

(RS)-[5-(1,3-Benzodioxol-5-ylmethoxy)-2-cyanophenoxy]-(2-methylphenyl)acetic Acid A stirred solution of (RS)-a-hydroxy-(2-methylphenyl) acetic acid (11 g) and Reference Example 36 (14.4 g) in dry dimethyl sulphoxide (100 ml), at room temperature, was treated portionwise with sodium hydride (5.94 g, 60% dispersion in mineral oil) over 1 hour. After stirring for 18 hours at ambient temperature the reaction mixture was evaporated and the residue dissolved in water (500 ml). The solution was washed three times with ethyl acetate (100 ml), and the aqueous phase was acidified to pH 1.5 and extracted three times with ethyl acetate (300 ml). The combined extracts were dried over magnesium sulphate, evaporated and the residual brown gum purified by flash chromatography on silica eluting with a mixture of ethyl acetate and pentane (3:2, v/v). Three of the fractions containing the required product were combined and evaporated. The residual pale yellow solid was triturated with a mixture of diisopropyl ether and pentane affording the title compound (6.85 g) as a cream coloured solid, m.p. 125–126° C. [Elemental analysis:-C,69.06; H,4.59; N,3.36%. Calculated:-C,68.65; H,4.66; N,3.28%]. Two latter fractions containing the required product were combined and evaporated. The residual pale yellow solid was triturated with a mixture of diisopropyl ether and pentane affording a further 3.8 g of the title compound as a cream coloured solid, m.p. 124–125° C. [Elemental analysis:-C,68.47; H,4.80; N,3.27%. Calculated for $C_{24}H_{19}NO_6.0.1H_2O$:-C,68.71; H,4.62; N,3.34%].

EXAMPLE 20

(RS)-(2-Chlorophenyl)-[2-cyano-5-(isothiazol-4-ylmethoxy)phenoxy]acetic Acid

A solution of Reference Example 37 (0.43 g) in dioxan (30 ml) was treated with 1 N sodium hydroxide (3 ml) and stirred at ambient temperature for 2 hours. The reaction mixture was evaporated, water (10 ml) was added to the residue and the solution washed with ether (15 ml), then acidified to pH 1 with 2 N hydrochloric acid. The mixture was extracted twice with ethyl acetate (40 ml). The combined extracts were washed twice with water (15 ml), then with brine (15 ml), dried over magnesium sulphate and evaporated. The residual gum was triturated with a mixture of pentane and ether (20 ml, 2:1, v/v) affording the title compound (0.34 g) as a white solid, m.p. 194–197° C.

EXAMPLE 21

(RS)-[2-Cyano-5-(3-pyridylmethoxy)phenoxy]-phenylacetic Acid

A solution of Reference Example 38 (0.2 g) in dioxan (10 ml) was treated with 1 N sodium hydroxide (1.2 ml) and stirred at ambient temperature for 2 hours. The reaction mixture was acidified to pH 5 with 2 N hydrochloric acid and extracted with ethyl acetate. The organic extracts were washed with brine, dried over magnesium sulphate, evaporated and the residue purified by flash chromatography on silica eluting with a mixture of pentane and ethyl acetate (3:1, v/v). Fractions homogenous in the required product were combined and evaporated affording the title compound (0.39 g) as a yellow solid, m.p. 201–202° C.

EXAMPLE 22

(RS)-[2-Formyl-5-(3-thienylmethoxy)phenoxy]-phenylacetic Acid

A solution of Reference Example 42 (0.50 g) in dioxan (10 ml) was treated with 1 N sodium hydroxide (3.63 ml) and stirred at 25° C. for 2 hours. The solution was treated with water (40 ml), acidified to pH 2 with 3 N hydrochloric acid and extracted three times with ethyl acetate (75 ml). The combined extracts were washed with brine (70 ml), dried and evaporated. The residue was triturated with ether to give the title compound (0.17 g) as a cream solid, m.p. 172–174° C. [Elemental analysis:-C,64.2; H,4.34%. Calculated for $C_{20}H_{16}O_5S.0.33H_2O$:-C,64.2; H,4.49%].

EXAMPLE 23

(RS)-N-{[2-Cyano-5-(3-thienylmethoxy)phenoxy] phenylacetyl}-4-isopropylbenzenesulphonamide A solution of Example 2 (0.73 g) in dry dichloromethane (50 ml) was treated with N,N' carbonyldiimidazole (0.36 g) and stirred at 25° C. for 2 hours, when evolution of carbon dioxide was complete. A solution of 4-isopropylbenzenesulphonamide (0.60 g) in dry dimethylformamide (20 ml) was treated with sodium hydride (0.13 g, 60% dispersion in mineral oil) and stirred at 25° C. for 2 hours. This solution was then treated dropwise with the solution of acylimidazole prepared above and stirring was continued at 25° C. for 8 hours. The reaction mixture was evaporated, the residue diluted with water (50 ml) and extracted twice with ethyl acetate. The extracts were washed with water, dried and evaporated to give an orange oil which was purified by flash chromatography on silica eluting with ether. Fractions homogenous in the required product were combined and evaporated. The residual pale yellow solid (0.35 g) was recrystallized from a mixture of ethyl acetate and pentane affording the title compound (0.20 g) as colourless crystals, m.p. 187–189° C. [Elemental analysis:-C,63.7; H,4.79; N,5.12%. Calculated:-C,63.7; H,5.17; N,5.17%].

EXAMPLE 24

(RS)-[2-Cyano-5-(4-pyridylmethoxy)phenoxy]-(2-methylphenyl)acetic Acid, Acetoxy Methyl Ester A mixture of Example 13 (0.6 g) in dimethylformamide (50 ml) was treated at room temperature under argon with sodium hydride (0.072 g, 60% dispersion in oil) and stirred for 30 minutes. Bromomethyl acetate (0.24 ml) was added and the mixture stirred 2 hours. The reaction mixture was evaporated and the residue purified by flash chromatography on silica eluting with a mixture of dichloromethane and methanol (99:1, v/v). Fractions homogenous in the required product were combined and evaporated. The residue was triturated with pentane affording the title compound (0.34 g) as a white solid, m.p. 127–130° C. [Elemental analysis:-C, 67.13; H,4.83; N,6.24%; Calculated:-C,67.26; H,4.97; N,6.27%].

EXAMPLE 25

Sodium (S)-[2-cyano-5-(4-pyridylmethoxy) phenoxy]-(2-methylphenyl)acetate

A suspension of Example 17 (19.5 g) in water (195 ml) was treated with 0.1 N sodium hydroxide (510 ml) and stirred at 25° C. for 15 minutes. The mixture was filtered from a trace of insoluble solid and the filtrate was freeze dried. The residue was triturated with ether, dried at 50° C./0.1 mm/2 hour and equilibrated 25° C./760 mm/2 days, giving the title compound (15.0 g) as a colourless solid, m.p. 191–193° C.(dec), softens at 130° C. [Elemental analysis:-C,63.8; H,4.49; N,6.59; $H_2O$,4.71%. Calculated for $C_{22}H_{17}N_2O_4Na.H_2O$:-C,63.8; H,4.62; N,6.76; $H_2O$,4.35%].

EXAMPLE 26

Sodium (S)-[5-(1,3-benzodioxol-5-ylmethoxy)-2-cyanophenoxy]-(2-methylphenyl)acetate Method A: A suspension of Example 35(a) (13.5 g) in water (50 ml) was treated with 0.1 N sodium hydroxide (320 ml) and stirred at 25° C. for 30 minutes. The mixture was filtered from a trace of insoluble solid, the filtrate was freeze dried and the solid recrystallized from butanol affording the title compound (8.15 g) as a white solid, m.p. 218–222° C. [Elemental analysis:-C,65.5; H,4.15; N,3.38%. Calculated:-C,65.6; H,4.20; N,3.19%].

Method B: A suspension of Reference Example 72(a) (8.0 g) in ethyl acetate (80 ml) was stirred for 10 minutes with sulphuric acid (1 N; 21 ml) at about 20° C. The two layers were separated; the ethyl acetate solution was washed twice with water (20 ml), filtered and the filtrate was diluted with methanol (24 ml). Aqueous sodium hydroxide (9 N; about 1.5 ml) was added until the solution reached pH 8.5–9 by pH paper. The solution was concentrated by distillation of about 85 ml of volatile solvent. Ethyl acetate (80 ml) was added and the mixture further concentrated until crystallisation commenced (about 55 ml distilled). The mixture was stirred at about 20° C., then with ice-bath cooling until crystallisation was complete. The product was filtered, washed with tert-butyl methyl ether and dried by suction and then at about 50° C./300 mbar to give the title compound (4.63 g; ee>98%).

Method C: A suspension of Reference Example 72(a) (220.0 g) in ethyl acetate (1100 ml) was stirred for 30 minutes with sulphuric acid (2 N; 282 ml) at about 20° C. After about 5 minutes all the solid had dissolved. The two layers were filtered. The organic phase was separated and the ethyl acetate solution was washed with water (220 ml) and then with aqueous sodium chloride (220 ml). The organic solution was stirred with charcoal (11.0 g) then filtered and concentrated under reduced pressure. The residue was treated with toluene (300 ml) and concentrated under reduced pressure to leave of (S)-[5-(1,3-benzodioxol-5- ylmethoxy)-2-cyanophenoxy]-(2-methylphenyl)acetic acid (157.0 g) as a solid. The product was dissolved in ethanol (785 ml) with warming. Aqueous sodium hydroxide (9 N; about 42 ml) was added until the solution reached pH 8.5–9 by pH paper then butanol (1570 ml) and water (40 ml) were added.

This solution was combined with a solution prepared in a similar manner from (415.3 g) of Reference Example 72(a) and stirred with heating to about 80° C. and concentrated by reducing the pressure as necessary to maintain distillation at about this temperature until crystallisation had started. The mixture was left to cool to about 20° C., then filtered and washed with butanol (350 ml) and then with tert-butyl methyl ether (650 ml). The product was dried by suction and then at about 70° C./300 mbar to give the title compound (395.5 g; ee>99%).

EXAMPLE 27

(RS)-(2-Chlorophenyl)-[2-cyano-3-fluoro-5-(3-thienylmethoxy)phenoxy]acetic Acid

A solution of Reference Example 43 (0.95 g) in dioxan (30 ml) was treated with 1 N sodium hydroxide (25 ml) and stirred at ambient temperature for 4 hours. The reaction mixture was treated with a further quantity of 1 N sodium hydroxide solution (5 ml) and stirring continued for 30 minutes by which time tlc (dichloromethane:methanol, 19:1 v/v) indicated the reaction was complete. Water (100 ml) was added, the solution was washed diethyl ether (50 ml), then acidified to pH 1 by addition of 1 N hydrochloric acid. The mixture was extracted three times with diethyl ether (50 ml). The combined organic extracts were washed with brine (50 ml), dried over magnesium sulphate, and evaporated. The residual viscous yellow oil was crystallised from a mixture of ethyl acetate and cyclohexane affording the title compound (0.55 g) as a cream coloured solid, m.p. 152–153° C. [Elemental analysis:-C,57.78; H,3.17; N,3.35; S,7.41%. Calculated:-C,57.49; H,3.11; N,3.35; S,7.66%].

EXAMPLE 28

(RS)-[5-(Benzoxazol-6-ylmethoxy)-2-cyanophenoxy]-(2-chlorophenyl)acetic Acid

A solution of Reference Example 47 (0.9 g) in dioxan (10 ml) was treated with 1 N sodium hydroxide (5 ml) and stirred at ambient temperature for 1.25 hours. The pH of the resulting dark orange solution was adjusted to 8 by addition of 2 N hydrochloric acid and the reaction mixture concentrated under reduced pressure at 35° C. The residual gum was dissolved in water (10 ml), the solution acidified to pH 2.5 by addition of 2 N hydrochloric acid and extracted with ethyl acetate. The combined extracts were washed with water, with brine, dried over magnesium sulphate, and evaporated. The residual dark brown oil (1.4 g) was triturated with pentane (40 ml) then with diethyl ether (20 ml) giving a buff coloured solid (0.75 g) which was purified by flash chromatography on silica eluting with a mixture of dichloromethane and methanol (14:1, v/v). Fractions homogenous in the required product were combined and evaporated affording the title compound (0.08 g) as a buff coloured solid, m.p. 172–178° C. [Elemental analysis:-C, 62.70; H,3.63; N,6.25%. Calculated for $C_{23}H_{15}ClN_2O_5.0.32H_2O$:-C,62.7; H,3.58; N,6.36%].

EXAMPLE 29

(RS)-[2-Cyano-5-(4-pyridylmethoxy)phenoxy]-[2-(3-methyl)thienyl]acetic Acid

A mixture of Reference Example 49 (1.14 g) and 1 N sodium hydroxide (5.7 ml) in dioxan (50 ml) was stirred at room temperature overnight. Further sodium hydroxide (5 ml) was added and stirring was continued for a further 3 hours at room temperature. The clear solution was evaporated to dryness and the residue was azeotroped repeatedly with toluene. The resulting white powder was dissolved in anhydrous dimethyl sulphoxide (20 ml) under nitrogen and the solution was treated with sodium hydride (0.37 g, 60% dispersion in mineral oil). The mixture was stirred at room temperature for 30 minutes when Reference Example 32 (1.25 g) was added in one portion. After stirring for 1 hour at room temperature the reaction mixture was partitioned between ethyl acetate (100 ml) and 5% aqueous sodium bicarbonate solution (100 ml). The aqueous phase was acidified to pH 5 by addition of acetic acid and extracted with ethyl acetate (100 ml). The ethyl acetate extract was washed with water (50 ml), dried over magnesium sulphate and evaporated. The residue was recrystallized from ethyl acetate affording the title compound (0.26 g) as a white solid; m.p. 153–154° C. [Elemental Analysis:-C,61.3; H,4.25; N,7.21; S,8.09%. Calculated for $C_{20}H_{16}N_2O_4S.0.5H_2O$:-C,61.7; H,4.37; N,7.20; S,8.23%].

EXAMPLE 30

(RS)-[(2-Cyano-5-(thiazol-5-ylmethoxy)phenoxy]-(2-methylphenyl)acetic Acid (RS)-α-Hydroxy-(2-methylphenyl)acetic acid (0.44 g) was added portion wise to a stirred suspension of sodium hydride (0.32 g, 60% suspension in mineral oil) in anhydrous dimethyl sulphoxide (10 ml). Reference Example 50 (0.62 g) was added in one portion and the mixture stirred at room temperature for 1 hour. The reaction mixture was partitioned between ethyl acetate (100 ml) and 5% aqueous sodium hydrogen carbonate solution (100 ml). The aqueous layer was washed with ethyl acetate (20 ml), acidified to pH 5 by the addition of acetic acid and extracted with ethyl acetate. The extract was washed with water (10 ml), dried over magnesium sulphate, and evaporated. The residue was recrystallized from a mixture of ethyl acetate and cyclohexane affording the title compound (0.25 g), m.p. 226–227° C. [Elemental analysis:-C,60.5; H,4.28; N,6.85; S,7.35%. Calculated for $C_{20}H_{16}N_2O_4S.H_2O$:-C,60.3; H,4.52; N,7.04; S,8.04%].

EXAMPLE 31

(RS)-(2-Chlorophenyl)-[2-cyano-3-fluoro-5-(4-pyridylmethoxy)phenoxy]acetic Acid

A solution of Reference Example 51 (0.72 g) in dioxan (20 ml) and 1 N sodium hydroxide (2 ml) was stirred at room temperature for 30 minutes. The solution was diluted with water (50 ml) and washed with diethyl ether (40 ml). The aqueous layer was acidified to pH 4 by addition of 1 N hydrochloric acid and extracted three times with diethyl ether (40 ml). The combined organic extracts were washed with saturated brine (50 ml), dried over magnesium sulphate and evaporated. The residual yellow gum was triturated with a mixture of diethyl ether and ethyl acetate (1:1, v/v) affording the title compound (0.7 g) as a cream solid, m.p. 135–139° C. [Elemental analysis:-C,60.93; H,3.70; N,6.64%. Calculated:-C,61.09; H,3.39; N,6.79%].

EXAMPLE 32

(RS)-2-[(2-Chlorophenyl)-(1H-tetrazol-5-yl) methoxy]-4-(4-pyridylmethoxy)benzonitrile A solution of Reference Example 58 (0.6 g) in dry dimethyl sulphoxide (20 ml) under nitrogen was treated with sodium hydride (0.23 g, 60% dispersion in mineral oil). After stirring at ambient temperature for 5 minutes Reference Example 32 (0.65 g) was added and stirring continued for 45 minutes. Water (100 ml) was added, the mixture was acidified to pH 4 by addition of 1 N hydrochloric acid and extracted three times with a mixture of ethyl acetate and methanol (60 ml, 9:1 v/v). The separating funnel had to be washed with methanol at this stage to dissolve some insoluble material. The combined extracts and methanol washings were concentrated and the residue diluted with water (100 ml) and the pH of this solution adjusted to 4 by addition of 1 N hydrochloric acid. The resulting solid was filtered and dried affording the title compound (0.91 g), as an off white solid m.p. 108–110° C. [Elemental analysis:-C, 55.58; H,3.81; N,18.6%. Calculated for $C_{21}H_{15}ClN_6O_2.1.5H_2O$:-C,56.0; H,4.10; N,18.66%].

EXAMPLE 33

(RS)-[3-Chloro-2-cyano-5-(4-pyridylmethoxy) phenoxy]-(2-chlorophenyl)acetic Acid A solution of Reference Example 60 (0.3 g) in dioxan (20 ml) was treated with 1 N sodium hydroxide (5 ml) and stirred at room temperature for 1 hour. After standing at room temperature for 48 hours the solution was diluted with water (30 ml) and washed with diethyl ether (30 ml). The aqueous layer was acidified to pH 4 by addition of 1 N hydrochloric acid and extracted three times with a mixture of methanol and ethyl acetate (40 ml, 1:9, v/v). The combined organic extracts were washed with saturated brine (40 ml), dried over magnesium sulphate and evaporated affording the title compound (0.15 g) as a cream solid, m.p. 165–167° C. [Elemental analysis:-C,57.85; H,3.59; N,6.29%. Calculated for $C_{21}H_{14}Cl_2N_2O_4.0.5CH_3OH$:-C, 57.97; H,3.39; N,6.79%].

EXAMPLE 34

(RS)-[5-(Benzoxazol-6-ylmethoxy)-2-cyanophenoxy]-(2-methylphenyl)acetic Acid

A solution of Reference Example 69 (0.9 g) in dioxan (10 ml) was treated with 1 N sodium hydroxide (5 ml) and stirred at ambient temperature for 1.25 hours. The pH of the resulting dark orange solution was adjusted to 8 by addition of 2 N hydrochloric acid and the reaction mixture concentrated under reduced pressure at 35° C. The residual gum was dissolved in water (10 ml), the solution acidified to pH 2.5 by addition of 2 N hydrochloric acid and extracted with ethyl acetate. The combined extracts were washed with water, with brine, dried over magnesium sulphate, and evaporated. The residual dark brown oil (1.4 g) was triturated with pentane (40 ml) then with diethyl ether (20 ml) giving a buff coloured solid (0.75 g) which was purified by flash chromatography on silica eluting with a mixture of dichloromethane and methanol (14:1, v/v). Fractions homogenous in the required product were combined and evaporated affording the title compound as a buff coloured solid, m.p. 172–178° C. [Elemental analysis:-C,62.70; H,3.63; N,6.25%. Calculated for $C_{23}H_{15}ClN_2O_5.0.32H_2O$:-C,62.7; H,3.58; N,6.36%].

EXAMPLE 35

(a) (S)-[5-(1,3-Benzodioxol-5-ylmethoxy)-2-cyanophenoxy]-(2-methylphenyl)acetic Acid A stirred suspension of Reference Example 72(a) (0.58 g) in ethyl acetate (50 ml) was treated with 2 N hydrochloric acid (20 ml). After stirring at ambient temperature for 40 minutes the organic layer was separated, washed with 2 N hydrochloric acid (20 ml) then with brine (20 ml), dried over magnesium sulphate and evaporated. The residue was triturated with a mixture of ether and pentane affording the title compound (0.24 g) as a glassy white solid, m.p. 52–56° C. $[\alpha]_D^{20}$+118° (c=0.005, methanol). [Elemental analysis:-C, 69.09; H,4.71; N,3.33%. Calculated:-C,69.06; H,4.59; N,3.36%].

(b) by proceeding in a similar manner to Example 35(a) but using Reference Example 72(b), may be prepared (S)-[5-(1,3-benzodioxol-5-ylmethoxy)-2-cyano-3-fluorophenoxy]-(2-methylphenyl)acetic acid.

EXAMPLE 36

(RS)-[5-(1,3-Benzodioxol-5-ylmethoxy)-2-cyanophenoxy]-(2-methylphenyl)acetic Acid A suspension of Reference Example 73 (123 g) in dioxan (1000 ml) was treated with 1 N sodium hydroxide (600 ml). After stirring at room temperature for 2 hours the reaction mixture was evaporated, the residue diluted with water (750 ml) and the mixture washed with ethyl acetate (200 ml). The aqueous phase was acidified to pH 1 by addition of concentrated hydrochloric acid and extracted twice with ethyl acetate (250 ml). The combined extracts were evaporated and the residue triturated with a mixture of ethyl acetate and cyclohexane affording the title compound (99.6 g) as a beige solid, m.p. 124–126° C.

EXAMPLE 37

(RS)-2-Cyano-[5-(4-(3-fluoropyridyl)methoxy) phenoxy]-(2-methylphenyl)acetic Acid A solution of Reference Example 74 (0.15 g) in dioxan (10 ml) was treated with 1 N sodium hydroxide (0.5 ml) and stirred at ambient temperature for 3.5 hours. A further quantity of 1 N sodium hydroxide (0.5 ml) was added and stirring continued for 1 hour. The reaction mixture was diluted with water (50 ml), the pH adjusted to 3 by addition of 2 N hydrochloric acid and mixture extracted three times with ethyl acetate (25 ml). The combined extracts were washed with brine (25 ml), dried over magnesium sulphate, and evaporated. The residue was triturated with diisopropyl ether and the resulting pale yellow solid washed with pentane. Recrystallization from a mixture of ethyl acetate and pentane afforded the title compound (0.75 g) as white crystalline solid, m.p. 178–179° C. [Elemental analysis:-C, 67.31; H,4.44; N,7.12%. Calculated:-C,66.34; H,4.37; N,7.14%].

EXAMPLE 38

(RS)-2-[(2-Methylphenyl)-(1H-tetrazol-5-yl) methoxy]-4-(4-pyridylmethoxy)benzonitrile A stirred solution of Reference Example 76 (0.42 g) in dry dimethyl sulphoxide (10 ml) under a nitrogen atmosphere at room temperature was treated with sodium hydride (0.19 g, 60% dispersion in mineral oil). After stirring at ambient temperature for 30 minutes Reference Example 32 (0.5 g) was added and stirring continued 5 hours. Water (50 ml) was added, the mixture washed with diethyl ether (50 ml) and the pH of the aqueous phase adjusted to 4 with 1 N hydrochloric acid. The resulting solid was washed twice with water (10 ml) affording the title compound (0.34 g) as a cream solid, m.p. 132–133° C. [NMR{$(CD_3)_2SO$}:-2.3 (s,3H), 5.2

(s,2H), 6.8 (dd,1H), 7.0 (d,1H), 7.25 (m,4H), 7.4 (dd,2H), 7.5 (dd,1H), 7.7 (d,1H), 8.6 (dd,2H)].

EXAMPLE 39

(RS)-4-(1,3-Benzodioxol-5-ylmethoxy)-2-[(2-methylphenyl)-(1H-tetrazol-5-yl)methoxy] benzonitrile A stirred solution of Reference Example 76 0.34 g) in dry dimethyl sulphoxide (10 ml) under nitrogen at room temperature was treated with sodium hydride (0.16 g, 60% dispersion in mineral oil). After stirring at room temperature for 30 minutes a solution of Reference Example 36 (0.5 g) in dry dimethyl sulphoxide (5 ml) was added and stirring continued for 18 hours. Water (50 ml) was added, the mixture was washed with diethyl ether (50 ml) and the pH of the aqueous phase adjusted to 2 by addition of 1 N hydrochloric acid. The mixture was extracted four times with diethyl ether (50 ml) and once with ethyl acetate (10 ml). The combined organic extracts were washed three times with water (50 ml), dried over magnesium sulphate and evaporated. Recrystallization from a mixture of cyclohexane and ethyl acetate gave the title compound (0.49 g) as a white solid, m.p. 106–109° C. [Elemental analysis:-C,66.04; H,4.64; N,15.47%. Calculated:-C,65.30; H,4.34; N,15.86%].

EXAMPLE 40

(RS)-[2-Cyano-3-fluoro-5-(4-pyridylmethoxy) phenoxy]-(2-methylphenyl)acetic Acid A solution of Reference Example 78 (0.64 g) in dioxan (20 ml) and 1 N sodium hydroxide (5 ml) was stirred at room temperature for 30 minutes. The solution was diluted with water (50 ml) and washed with diethyl ether (50 ml). The aqueous phase was acidified to pH 4 by addition of 1 N hydrochloric acid and extracted twice with diethyl ether (50 ml). The combined organic extracts were washed with saturated brine (50 ml), dried over magnesium sulphate and evaporated. The residual yellow gum was triturated with diethyl ether affording the title compound (0.10 g) as a cream solid, m.p. 163–165° C. [NMR {(CD$_3$)$_2$SO}:-2.4 (s,3H), 5.3 (s,2H), 6.3 (s,1H), 6.9 (m,2H), 7.3 (m,3H), 7.5 (m,3H), 8.6 (dd,2H)].

EXAMPLE 41

(RS)-[5-(Benzoxazol-6-ylmethoxy)-2-cyano-3-fluorophenoxy]-(2-methylphenyl)acetic Acid A solution of Reference Example 81 (0.35 g) in dioxan (20 ml) and 1 N sodium hydroxide (3 ml) was stirred at room temperature for 1 hour then stood at ambient temperature for 18 hours. The reaction mixture was evaporated to low volume, diluted with water (50 ml) and washed with diethyl ether (50 ml). The aqueous phase was acidified to pH 6 by addition of 1 N hydrochloric acid and extracted three times with ethyl acetate (50 ml). The combined organic extracts were washed with saturated brine (50 ml), dried over magnesium sulphate and evaporated. The resulting orange solid was triturated with methanol affording the title compound (0.24 g) as an orange solid, m.p. 193–194° C. [Elemental analysis:-C,65.93; H,4.0; N,5.9%. Calculated for C$_{24}$H$_{17}$N$_2$O$_5$F.0.5CH$_3$OH:-C,66.63; H,4.24; N,6.25%].

EXAMPLE 42

(RS)-[5-(1,3-Benzodioxol-5-ylmethoxy)-2-cyano-3-fluorophenoxy]-(2-methylphenyl)acetic Acid A solution of Reference Example 82 (1.42 g) in dioxan (20 ml) and 1 N sodium hydroxide (5 ml) was stirred at room temperature for 5 hours. The mixture was evaporated to low volume and was diluted with water (50 ml) and washed with diethyl ether (50 ml). The aqueous phase was acidified to pH 6 by addition of 1 N hydrochloric acid and extracted once with diethyl ether (50 ml) and twice with ethyl acetate (50 ml). The combined organic extracts were washed with saturated brine (50 ml), dried over magnesium sulphate and evaporated. The resulting colourless oil was triturated with pentane affording the title compound (0.65 g) as a cream solid, m.p. 110–117° C. [NMR (CDCl$_3$):-2.5 (s,3H), 4.9 (s,2H), 5.8 (s,1H), 6.0 (s,2H), 6.2 (m,1H), 6.4 (dd,1H), 6.8 (m,3H), 7.3 (m,3H), 7.6 (dd,1H)].

EXAMPLE 43

(RS)-[5-(Benzoxazol-5-yl)methoxy-2-cyanophenoxy]-(2-methylphenyl)acetic Acid

A solution of Reference Example 83 (0.12 g) in dioxan (10 ml) was treated with 1 N aqueous sodium hydroxide (1 ml) at room temperature. After 3 hours water was added (20 ml) and the mixture extracted with ethyl acetate (20 ml). The resulting aqueous layer was acidified to pH 1 by addition of concentrated hydrochloric acid and extracted three times with ethyl acetate (25 ml). The combined extracts were washed with brine (25 ml), dried over magnesium sulphate and evaporated. The resulting residue was recrystallized from ethyl acetate to give the title compound (80 mg) as a white solid, m.p. 189–191° C. [Elemental analysis:-C,68.03; H,4.49; N,6.34%. Calculated for C$_{24}$H$_{18}$N$_2$O$_5$.0.5H$_2$O:-C, 68.10; H,4.52; N,6.62%].

EXAMPLE 44

(RS)-(5-Benzyloxy-2-cyanophenoxy)-(2-methylphenyl)acetic Acid

A solution of Reference Example 85 (0.49 g) in dioxan (10 ml) was treated with 1 N aqueous sodium hydroxide (3 ml) at room temperature. After 30 minutes water was added (20 ml) and the mixture extracted with ethyl acetate (20 ml). The resulting aqueous layer was acidified to pH 1 by addition of concentrated hydrochloric acid and extracted three times with ethyl acetate (25 ml). The combined extracts were washed with brine (25 ml), dried over magnesium sulphate and evaporated. The resulting residue was purified by flash chromatography on silica eluting with a mixture of methanol and dichloromethane (1:19, v/v). Fractions homogenous in the required product were combined and evaporated. The resulting residue was triturated with diethyl ether and pentane to give the title compound (80 mg) as a white solid, m.p. 128–130° C. [Elemental analysis:-C, 73.91; H,5.26; N,3.69%. Calculated:-C,73.98; H,5.13; N,3.75%].

EXAMPLE 45

(RS)-[2-Cyano-5-(furan-3-ylmethoxy)phenoxy]-(2-methylphenyl)acetic Acid

A solution of Reference Example 86 (1.01 g) in dioxan (20 ml) was treated with 1 N aqueous sodium hydroxide (8 ml) at room temperature. After 1 hour the resulting solution was evaporated, the residue diluted with water (10 ml) and the pH adjusted to 2 by addition of 2 N aqueous hydrochloric acid. The resulting mixture was extracted twice with ethyl acetate (20 ml). The combined extracts were washed with water, dried over magnesium sulphate, evaporated and the residue dissolved in 1 N aqueous sodium hydroxide (30 ml).

EXAMPLE 46

(RS)-N-Methoxy-[2-cyano-5-(3-thienylmethoxy) phenoxy]-(2-methylphenyl)acetamide

The solution was washed twice with ether (40 ml), adjusted to pH 1 by addition of 2 N aqueous hydrochloric acid and extracted three times with ethyl acetate (30 ml). The combined extracts were dried over magnesium sulphate and evaporated to give a colourless solid (0.29 g). Recrystallization from diisopropylether gave the title compound (0.18 g) as colourless crystals, m.p. 141–143° C. [Elemental analysis:-C,69.5; H,4.81; N,4.12%. Calculated:-C,69.4; H,4.72; N,3.86%].

A solution of Example 6 (0.37 g) in dichloromethane (10 ml) was treated with oxalyl chloride (0.28 g) and refluxed for 3 hours. After allowing to cool to room temperature the reaction mixture was concentrated. The resulting residue was re-dissolved in dichloromethane (15 ml), treated with triethylamine (0.15 ml) and methoxyamine hydrochloride (0.09 g). After stirring at room temperature for 2 hours the reaction mixture was evaporated to dryness, diluted with water (50 ml) and the mixture extracted twice with ethyl acetate (50 ml). The combined organic extracts were washed with brine (30 ml), dried over magnesium sulphate and evaporated. The resulting residue was purified by flash chromatography on silica eluting with a mixture of ethyl acetate and pentane (1:1, v/v). Fractions homogenous in the required product were combined and evaporated. The resulting residue was triturated with diethyl ether to give the title compound (0.1 g) as a white solid, m.p. 155–156° C. [Elemental analysis:-C,64.69; H,5.13; N,6.61%. Calculated:-C,64.69; H,4.94; N,6.86%].

REFERENCE EXAMPLE 1

4-Allyloxy-2-hydroxybenzaldehyde

A mixture of 2,4-dihydroxybenzaldehyde (15 g), allyl bromide (9.6 ml), potassium carbonate (15.4 g), potassium iodide (18.5 g) and tetra-n-butylammonium bromide (3.59 g) in methyl ethyl ketone (200 ml) was heated at reflux for 1 hour. The reaction mixture was filtered and evaporated. The residue was partitioned between ethyl acetate (100 ml) and water (100 ml). The organic phase was evaporated and the residual oil (20 g) purified by flash chromatography on silica eluting with a mixture of pentane and ethyl acetate (95:5, v/v). Fractions homogenous in the required product were combined and evaporated to give the title compound (13.8 g) as an oil.

REFERENCE EXAMPLE 2

4-Allyloxy-2-hydroxybenzaldehyde Oxime

A mixture of Reference Example 1 (7.48 g), hydroxylamine hydrochloride (3.32 g) and pyridine (3.12 ml) in ethanol (100 ml) was heated at reflux for 1 hour. The reaction mixture was evaporated and partitioned between ethyl acetate (100 ml) and water (100 ml). The organic phase was dried over magnesium sulphate and evaporated to low volume when pentane (80 ml) was added to give the title compound (5.5 g) as a colourless solid, m.p. 74–76° C.

REFERENCE EXAMPLE 3

2-Acetoxy-4-allyloxybenzonitrile

A mixture of Reference Example 2 (11.75 g), sodium acetate (0.2 g) and acetic anhydride (100 ml) was heated at reflux for 3 hours, cooled, carefully diluted with water (600 ml) with stirring and extracted three times with ethyl acetate (200 ml). The combined extracts were washed with water (150 ml), then with brine (150 ml), dried over magnesium sulphate and evaporated. The residual pale orange oil was purified by flash chromatography on silica eluting initially with a mixture of ethyl acetate and pentane (1:9, v/v) then with a mixture of ethyl acetate and pentane (15:85, v/v). Fractions homogenous in the required product were combined and evaporated to give the title compound (13.7 g) as a pale yellow oil.

REFERENCE EXAMPLE 4

4-Allyloxy-2-hydroxybenzonitrile

A solution of Reference Example 3 (13.7 g) in a mixture of methanol (15 ml) and tetrahydrofuran (50 ml) was treated, at room temperature, with a solution of potassium carbonate (8.72 g) in water (100 ml). After 2 hours, the reaction mixture was diluted with water (100 ml), acidified to pH 1 by addition of 2 N hydrochloric acid and extracted three times with ethyl acetate (200 ml). The combined organic extracts were washed with brine (200 ml), dried over magnesium sulphate and evaporated. The resulting off-white solid was recrystallized from diisopropyl ether to give the title compound (4.7 g) as an off-white solid, m.p. 134–136° C.

REFERENCE EXAMPLE 5

Methyl (RS)-(5-allyloxy-2-cyanophenoxy)-(2-chlorophenyl)acetate

A mixture of Reference Example 4 (3.31 g), Reference Example 10 (3.31 g) and potassium carbonate (2.37 g) in dimethylformamide (20 ml) was stirred at ambient temperature for 2 hours. The reaction mixture was diluted with water (30 ml), acidified to pH 2 by addition of concentrated hydrochloric acid and extracted three times with ethyl acetate (40 ml). The combined extracts were washed with brine (30 ml), dried over magnesium sulphate and evaporated. The residue was purified by flash chromatography on silica eluting with a mixture of ethyl acetate and pentane (1:4, v/v). Fractions homogenous in the required product were combined and evaporated to give the title compound (1.15 g).

REFERENCE EXAMPLE 6

Methyl (RS)-(2-chlorophenyl)-[2-cyano-5-hydroxyphenoxy]acetate

A stirred solution of Reference Example 5 (1.15 g) in a mixture of water (5 ml) and ethanol (50 ml) was treated with 1,4-diazabicyclo[2.2.2]octane (0.75 g) and tris(triphenylphosphine)rhodium(I) chloride (0.3 g). The reaction mixture was heated at reflux for 5 hours, evaporated to dryness and the residue partitioned between ethyl acetate (50 ml) and 2 N hydrochloric acid (50 ml). The aqueous phase was extracted with ethyl acetate (25 ml) and the combined organic phases were washed with brine, dried over magnesium sulphate and evaporated. The residue was purified by flash chromatography on silica eluting with a mixture of ethyl acetate and pentane (1:2, v/v). Fractions homogenous in the required product were combined and evaporated to give the title compound (0.62 g) as a yellow oil.

REFERENCE EXAMPLE 7

Methyl (RS)-(2-chlorophenyl)-[2-cyano-5-(4-pyridylmethoxy)phenoxy]acetate

A solution of Reference Example 6 (0.63 g) in acetone (25 ml) was treated with potassium carbonate (0.28 g) and 4-picolylchloride hydrochloride (0.36 g) and then stirred at reflux temperature for 24 hours. The reaction mixture was evaporated and the residue partitioned between ethyl acetate (100 ml) and water (75 ml). The organic phase was washed twice with 0.1 N sodium hydroxide (20 ml), then with brine (50 ml), dried over magnesium sulphate and evaporated. The residual oil slowly solidified on standing. The solid was stirred with ethyl acetate (30 ml), filtered and the filtrate evaporated to give the title compound (0.35 g) as a plum coloured waxy solid.

REFERENCE EXAMPLE 8

Methyl (RS)-[2-cyano-5-(3-thienylmethoxy)phenoxy]-phenylacetate

A solution of Reference Example 25 (1.0 g) in dimethylformamide (14 ml) was treated with sodium hydride (60% dispersion in mineral oil) and stirred at room temperature for 10 minutes. The solution was treated with methyl (RS)-$\mu$-bromophenylacetate (1.02 g) and stirred at 25° C. for 1 hour. The solution was diluted with water and extracted with ethyl acetate. The extract was washed with brine, dried and evaporated. The residue was washed with ether and recrystallized from a mixture of ethyl acetate and cyclohexane to give the title compound as a colourless solid (0.91 g), m.p. 112–114° C.

REFERENCE EXAMPLE 9

Methyl 2-chlorophenylacetate

A solution of 2-chlorophenylacetic acid (10.0 g) in methanol (100 ml) containing 1 drop of concentrated sulphuric acid was heated at reflux for 2 hours. The reaction mixture was evaporated to half volume and partitioned between ethyl acetate (100 ml) and water (100 ml). The organic phase was dried over magnesium sulphate and evaporated to give the title compound (10.0 g) as a colourless oil.

REFERENCE EXAMPLE 10

Methyl (RS)-a-bromo-(2-chlorophenyl)acetate

A mixture of Reference Example 9 (5.0 g), N-bromosuccinimide (5.3 g) and azobisisobutyronitrile (0.38 g) in dry chloroform (50 ml) was heated at reflux for 6 hours. The reaction mixture was washed three times with water (30 ml) and the organic phase dried over magnesium sulphate and evaporated. The residual oil was purified by flash chromatography on silica eluting with a mixture of ethyl acetate and pentane (5:95, v/v). Fractions homogenous in the required product were combined and evaporated to give the title compound (4.0 g) as an oil.

REFERENCE EXAMPLE 11

Methyl (RS)-(2-chlorophenyl)-[2-cyano-5-(3-thienylmethoxy)phenoxy]acetate

A solution of Reference Example 25 (2.0 g) in dimethylformamide (80 ml) was treated with sodium hydride (0.22 g, 60% dispersion in mineral oil) and stirred at ambient temperature for 10 minutes. The solution was treated with Reference Example 10 (1.7 g) and stirred at 25° C. for 1 hour. The reaction mixture was partitioned between ethyl acetate (100 ml) and water (100 ml). The organic phase was washed twice with brine (10 ml), dried over magnesium sulphate and evaporated. The residual oil was triturated with pentane (50 ml) to give the title compound (1.75 g) as a colourless solid, m.p.102–104° C. [Elemental analysis:-C, 60.97; H,3.88; N,3.31; S,7.16%. Calculated:-C,60.94; H,3.89; N,3.38; S,7.74%].

REFERENCE EXAMPLE 12

4-(1,3-Benzodioxol-5-ylmethoxy)-2-hydroxybenzaldehyde

A mixture of 2,4-dihydroxybenzaldehyde (22.94 g), 3,4-methylenedioxybenzyl chloride (34 g), potassium carbonate (34.43 g), potassium iodide (41.33 g) and tetra-n-butylammonium bromide (6 g) in methyl ethyl ketone was heated at reflux for 3 hours. The reaction mixture was filtered and evaporated. The residue was partitioned between ethyl acetate (400 ml) and water (400 ml) and the aqueous phase extracted twice with ethyl acetate (200 ml). The combined organic phases were dried over magnesium sulphate and evaporated. The residual beige coloured solid was purified by flash chromatography on silica eluting initially with a mixture of pentane and ethyl acetate (95:5, v/v) then with a mixture of pentane and ethyl acetate (9:1, v/v) and finally with a mixture of pentane and ethyl acetate (85:15, v/v). Fractions homogenous in the required product were combined and evaporated to give the title compound (14.2 g) as a white solid.

REFERENCE EXAMPLE 13

4-(1,3-Benzodioxol-5-ylmethoxy)-2-hydroxybenzaldehyde Oxime

A mixture of Reference Example 12 (3.9 g), hydroxylamine hydrochloride (0.99 g) and pyridine (1.25 ml) in ethanol (100 ml) was heated at reflux for 1.5 hours. The reaction mixture was partitioned between ethyl acetate (100 ml) and water (100 ml) and the aqueous phase was extracted twice with ethyl acetate (100 ml). The combined organic phases were washed with 1 N hydrochloric acid (100 ml), brine (100 ml), dried over magnesium sulphate and evaporated to give the title compound (2.6 g) as a white solid.

REFERENCE EXAMPLE 14

2-Acetoxy-4-(1,3-benzodioxol-5-ylmethoxy)benzonitrile

A mixture of Reference Example 13 (2.6 g), sodium acetate (0.03 g) and acetic anhydride (15 ml) was heated at reflux for 3.5 hours, allowed to cool to room temperature and stood for 3 days. The reaction mixture was carefully diluted with water (250 ml) with stirring and filtered. The insoluble material was recrystallized from a mixture of diisopropyl ether and ethyl acetate to give the title compound (1.52 g) as a cream coloured solid.

REFERENCE EXAMPLE 15

4-(1,3-Benzodioxol-5-ylmethoxy)-2-hydroxybenzonitrile

Method A: A solution of Reference Example 14 (1.5 g) in a mixture of methanol (15 ml) and tetrahydrofuran (7 ml) was treated, at room temperature, with a solution of potassium carbonate (0.66 g) in water (10 ml). The solution slowly turned reddish-brown and after 1 hour the reaction mixture was diluted with water (30 ml) and extracted three times with ethyl acetate (75 ml) The combined organic extracts were washed with brine (30 ml), dried over magnesium sulphate and evaporated to give the title compound (1.34 g) as a sand coloured solid.

Method B: A stirred suspension of Reference Example 12 (845.0 g) in ethanol (7770 ml) was treated with a solution of hydroxylamine-O-sulphonic acid (470.7 g) in demineralized water (1110 ml). The reaction mixture was stirred at 25–30° C. for about 1 hour forming a clear solution. The solution was cooled to about 5° C. then aqueous sodium hydroxide (1550 ml; 9.1 N) was added over about 3 hours keeping the temperature between 5° C. and 15° C. The mixture was then stirred at 5°–15° C. until the reaction was complete by thin layer chromatography (about 1–1.5 hours). Keeping the temperature below 30° C., the pH of the mixture was adjusted to 1–2 by addition of concentrated hydrochloric acid. The mixture was diluted with demineralized water (3900 ml) and stirred for 30 minutes at 25–30° C. The product was collected, washed with demineralized water (3900 ml) and dried by suction then at 45–50° C./500 to 750 Torr to give the title compound (760.0 g).

REFERENCE EXAMPLE 16

Methyl (RS)-[5-(1,3-benzodioxol-5-ylmethoxy)-2-cyano-phenoxy]-phenylacetate

A mixture of Reference Example 15 (1.3 g), methyl (RS)-a-bromophenylacetate (1.22 g) and potassium carbonate (1.0 g) in dimethylformamide (10 ml) was stirred at ambient temperature for 2 hours. Water (30 ml) was added and the solution acidified to pH 2 by addition of concentrated hydrochloric acid. The mixture was extracted three times with ethyl acetate (30 ml) and the combined extracts were washed with brine (30 ml), dried over magnesium sulphate and evaporated. On standing the title compound (0.77 g) was slowly deposited as a white solid.

REFERENCE EXAMPLE 17

Methyl 2-trifluoromethylphenylacetate

A solution of 2-trifluoromethylphenylacetic acid (5.0 g) in methanol (30 ml) containing 5 drops of concentrated sulphuric acid was heated at reflux for 2 hours. The reaction mixture was concentrated, diluted with ethyl acetate (100 ml), washed with 1 N sodium hydroxide (25 ml) then with brine (25 ml), dried over magnesium sulphate and evaporated to give the title compound (5.04 g) as a colourless oil.

REFERENCE EXAMPLE 18

Methyl (RS)-a-bromo-(2-trifluoromethylphenyl)acetate

A mixture of Reference Example 17 (5.0 g), N-bromosuccinimide (4.22 g) and azobisisobutyronitrile (0.33 g) in dry chloroform (40 ml) was heated at reflux for 18 hours. The reaction mixture was washed three times with water (25 ml) and the organic phase dried over magnesium sulphate and evaporated. The residual yellow oil was purified by flash chromatography on silica eluting with a mixture of ethyl acetate and pentane (1:3, v/v). Fractions homogenous in the required product were combined and evaporated to give the title compound (5.8 g) as a yellow oil.

REFERENCE EXAMPLE 19

Methyl (RS)-[5-(1,3-benzodioxol-5-ylmethoxy)-2-cyanophenoxy]-(2-trifluoromethylphenyl)acetate A mixture of Reference Example 15 (0.5 g), Reference Example 18 (0.58 g) and potassium carbonate (0.38 g) in dimethylformamide (5 ml) was stirred at ambient temperature for 1.5 hours. The reaction mixture was diluted with water (20 ml), acidified to pH 1 by addition of concentrated hydrochloric acid and extracted three times with ethyl acetate (20 ml). The combined extracts were washed with brine (20 ml), dried over magnesium sulphate and evaporated. The residual yellow semi-solid was triturated with ether to give the title compound (0.36 g) as a pale beige coloured solid.

REFERENCE EXAMPLE 20

Methyl (RS)-a-hydroxy-(2-methylphenyl)acetate

A solution of (RS)-a-hydroxy-(2-methylphenyl)acetic acid (3.6 g) in methanol (80 ml) containing 2 drops of concentrated sulphuric acid was heated at reflux for 2 hours. The reaction mixture was concentrated and the residual oil partitioned between ethyl acetate and water. The organic phase was washed with water, dried over magnesium sulphate and evaporated to give the title compound (2.5 g) as a colourless oil.

REFERENCE EXAMPLE 21

Methyl (RS)-a-bromo-(2-methylphenyl)acetate

Method A: To a stirred solution of Reference Example 20 (2.0 g) in dry dichloromethane (30 ml) at 0° C. was added triphenylphosphine (0.727 g) and carbon tetrabromide (0.92 g). The reaction mixture was stirred at ambient temperature for 3 hours and evaporated. The resulting oil was dissolved in ether and the solution filtered through a pad of silica washing the silica with ether. The combined filtrate and washings were evaporated and the residual oil was purified by flash chromatography on silica eluting with a mixture of ethyl acetate and pentane (1:4, v/v). Fractions homogenous in the required product were combined and evaporated to give the title compound (1.8 g) as a colourless oil.

Method B: A stirred solution of Reference Example 20 (63.2 g) in dry toluene (250 ml) at ambient temperature was treated with thionyl bromide (27 ml) and the mixture stood at ambient temperature for 3 days. The reaction mixture was washed with sodium bicarbonate solution until the washings were neutral, washed twice with brine (100 ml), dried over magnesium sulphate and evaporated affording the title compound (74.5 g) as a pale yellow oil.

REFERENCE EXAMPLE 22

Methyl (RS)-[2-cyano-5-(3-thienylmethoxy)phenoxy]-(2-methylphenyl)acetate

A solution of Reference Example 25 (0.7 g) in dimethylformamide (80 ml) was treated with sodium hydride (0.11 g, 60% dispersion in mineral oil) and stirred at ambient temperature for 40 minutes. The solution was treated with Reference Example 21 (0.726 g) and stirred at ambient temperature for 2 hours. The reaction mixture was concentrated and partitioned between ethyl acetate and water. The organic phase was washed with brine, dried over magnesium sulphate and evaporated. The residual oil was purified by flash chromatography on silica eluting with a mixture of ethyl acetate and pentane (1:4, v/v). Fractions homogenous in the required product were combined and evaporated, and the residual solid triturated with a mixture of pentane and ether to give the title compound (0.6 g) as a colourless solid, m.p. 102–104° C.

REFERENCE EXAMPLE 23

Methyl (RS)-[5-(1,3-benzodioxol-5-ylmethoxy)-2-cyanophenoxy]-(2-chlorophenyl)acetate A mixture of Reference Example 15 (1.5 g), Reference Example 10 (1.62 g) and potassium carbonate (1.16 g) in dimethylformamide (15 ml) was stirred at ambient temperature for 1.5 hours. The reaction mixture was diluted with water (30 ml), acidified to pH 2 by addition of concentrated hydrochloric acid and extracted three times with ethyl acetate (40 ml). The combined extracts were washed with brine (30 ml), dried over magnesium sulphate and evaporated. The residual yellow semi-solid was purified by flash chromatography on silica eluting initially with a mixture of ethyl acetate and pentane (1:4, v/v), then with a mixture of ethyl acetate and pentane (3:10, v/v). Fractions homogenous in the required product were combined and evaporated to give the title compound (0.36 g) as a colourless oil which slowly solidified on standing.

REFERENCE EXAMPLE 24

2-Hydroxy-4-(3-thienylmethoxy)benzaldehyde

A stirred solution of 2,4-dihydroxybenzaldehyde (31.8 g) in dry dimethylformamide (150 ml) at ambient temperature was treated with sodium hydride (11.96 g; 60% dispersion in mineral oil), portionwise, during 30 minutes. After a further period of 15 minutes, the mixture was treated, dropwise, with a solution of 3-chloromethylthiophene (35 g) in dimethylformamide (50 ml). The mixture was stirred at 70° C. for 2 hours, cooled and the solvent evaporated. The residue was partitioned between ethyl acetate (200 ml) and 0.5 N hydrochloric acid (200 ml) and the aqueous layer was extracted twice with ethyl acetate (100 ml). The combined organic phases were washed with brine (100 ml), dried over magnesium sulphate, and evaporated. The residue was subjected to flash chromatography on silica eluting with a mixture of ethyl acetate and pentane (1:4, v/v), to give a colourless oil, which crystallised on standing. This solid was recrystallized from diisopropyl ether, to give the title compound (8 g) as a white solid.

REFERENCE EXAMPLE 25

2-Hydroxy-4-(3-thienylmethoxy)benzonitrile

A mixture of Reference Example 24 (7.7 g), nitroethane (4.74 ml), sodium acetate (5.4 g) and glacial acetic acid (6.6 ml) was heated at reflux for 14 hours. The mixture was then cooled, diluted with water (50 ml) and extracted three times with ethyl acetate (50 ml). The combined extracts were washed with saturated aqueous sodium bicarbonate solution (50 ml), dried over magnesium sulphate and evaporated. The residue was subjected to flash chromatography on silica eluting with a mixture of ethyl acetate and pentane (3:7, v/v), to give the title compound (7.6 g) as a pale yellow solid.

REFERENCE EXAMPLE 26

Methyl 2-bromophenylacetate

A solution of 2-bromophenylacetic acid (5.6 g) in methanol (80 ml) containing 6 drops of concentrated sulphuric acid was heated at reflux for 12 hours. The reaction mixture was concentrated, dissolved in ether (100 ml) and washed with water. The ether solution was dried over magnesium sulphate and evaporated to give the title compound (5.8 g) as a light orange oil.

REFERENCE EXAMPLE 27

Methyl (RS)-a-bromo-(2-bromophenyl)acetate

A mixture of Reference Example 26 (2.29 g), N-bromosuccinimide (1.78 g) and azobisisobutyronitrile (0.145 g) in dry chloroform (25 ml) was heated at reflux for 6 hours. The reaction mixture was washed with brine and concentrated to give the title compound (2.9 g) as an orange oil.

REFERENCE EXAMPLE 28

Methyl (RS)-(2-bromophenyl)-[2-cyano-5-(3-thienylmethoxy)phenoxy]acetate

A solution of Reference Example 25 (0.693 g) in dimethylformamide (10 ml) was treated with sodium hydride (0.12 g, 60% dispersion in mineral oil) and stirred at ambient temperature for 15 minutes. The solution was treated with Reference Example 27 (1.7 g) and stirred at 25° C. for 1 hour. The reaction mixture was diluted with water (60 ml) and extracted with ethyl acetate. The organic extracts were washed with water, then with brine, dried over magnesium sulphate and evaporated. The residual oil was purified by flash chromatography on silica eluting with a mixture of pentane and ether (3:2, v/v). Fractions homogenous in the required product were combined and evaporated. The residue was triturated with ether to give the title compound (0.52 g) as a white solid, m.p. 92–95° C. [Elemental analysis:-C,55.17; H,3.58; N,3.10; S,7.37%. Calculated:-C, 55.03; H,3.52; N,3.06; S,6.99%].

REFERENCE EXAMPLE 29

Methyl 3-chlorophenylacetate

A solution of 3-chlorophenylacetic acid (10.0 g) in methanol (80 ml) containing 2 drops of concentrated sulphuric acid was heated at reflux for 3 hours. The reaction mixture was concentrated and partitioned between ethyl acetate (100 ml) and water (100 ml). The organic phase was dried over magnesium sulphate and evaporated to give the title compound (9.8 g) as a colourless oil.

REFERENCE EXAMPLE 30

Methyl (RS)-a-bromo-(3-chlorophenyl)acetate

A mixture of Reference Example 29 (5.0 g), N-bromosuccinimide (5.3 g) and azobisisobutyronitrile (0.38 g) in dry chloroform (50 ml) was heated at reflux for 6 hours. The reaction mixture was washed four times with water (50 ml) and the organic phase dried over magnesium sulphate and evaporated. The residual oil was purified by flash chromatography on silica eluting with a mixture of ethyl acetate and pentane (5:95, v/v). Fractions homogenous in the required product were combined and evaporated to give the title compound (4.3 g) as an oil.

REFERENCE EXAMPLE 31

Methyl (RS)-(3-chlorophenyl)-[2-cyano-5-(3-thienylmethoxy)phenoxy]acetate

A solution of Reference Example 25 (2.0 g) in dimethylformamide (80 ml) was treated with sodium hydride (0.22 g, 60% dispersion in mineral oil) and stirred at ambient temperature for 1 hour. The solution was treated with Reference Example 30 (1.7 g) and stirred at 25° C. for 2 hours. The reaction mixture was concentrated and partitioned between ethyl acetate (200 ml) and water (200 ml). The organic phase was washed twice with water (50 ml) then with brine (50 ml), dried over magnesium sulphate and evaporated. The residual oil was purified by flash chromatography on silica eluting with a mixture of ethyl acetate and pentane (1:4, v/v). Fractions homogenous in the required product were combined and evaporated to give the title compound (1.0 g).

REFERENCE EXAMPLE 32

2-Fluoro-4-(4-pyridylmethoxy)benzonitrile

A mixture of 2-fluoro-4-hydroxybenzonitrile (10.96 g; S. M. Kelly, Helv. Chim. Acta 1984, volume 67, p1572–1579), potassium carbonate (53.2 g), potassium iodide (6.64 g), tetra-n-butylammonium bromide (0.4 g) and 4-picolyl chloride (14.4 g) in methyl ethyl ketone (600 ml) was stirred at reflux for 3 hours. The reaction mixture was filtered and the insoluble material washed with methyl ethyl ketone. The combined filtrate plus washings were evaporated and the residue partitioned between ethyl acetate (300 ml) and water (150 ml). The aqueous phase was extracted twice with ethyl acetate (100 ml) and the combined ethyl acetate solutions washed with brine (100 ml), dried over magnesium sulphate and evaporated. The residue was recrystallized from a mixture of ethyl acetate and pentane to give the title compound (11.5 g) as a plum coloured solid, m.p. 132–133° C.

REFERENCE EXAMPLE 33

Methyl (RS)-[2-cyano-5-(3-thienylmethoxy) phenoxy]-(2-fluorophenyl)acetate

A solution of Reference Example 25 (0.693 g) in dimethylformamide (10 ml) was treated with sodium hydride (0.12 g, 60% dispersion in mineral oil) and stirred at ambient temperature for 30 minutes. The solution was treated with methyl (RS)-a-bromo-(2-fluorophenyl)acetate (1.8 g) and stirred at ambient temperature for 2 hours. The reaction mixture was concentrated and partitioned between ethyl acetate and water. The organic phase was washed with brine, dried over magnesium sulphate and evaporated. The residual brown oil (1.8 g) was purified by flash chromatography on silica eluting with dichloromethane. Fractions homogenous in the required product were combined and evaporated. The residual solid was triturated with a mixture of pentane and ether affording the title compound (0.75 g) as a white solid, m.p. 104–106° C. [Elemental analysis:-C,63.71; H,4.09; N,3.8; S,7.8%. Calculated:-C,63.47; H,4.06; N,3.53; S,8.07%]

REFERENCE EXAMPLE 34

Methyl (RS)-[2-cyano-5-(3-thienylmethoxy) phenoxy]-(2-trifluoromethylphenyl)acetate A solution Reference Example 25 (1.5 g) in dimethylformamide (100 ml) was treated with sodium hydride (0.24 g, 60% dispersion in mineral oil) and stirred at ambient temperature for 30 minutes. The solution was treated with Reference Example 18 (1.8 g) and stirred at ambient temperature for 2 hours. The reaction mixture was concentrated and partitioned between ethyl acetate (100 ml) and water (100 ml). The organic phase was washed with brine, dried over magnesium sulphate and evaporated. The residual oil (0.98 g) was purified by flash chromatography on silica eluting with a mixture of ethyl acetate and pentane (1:4, v/v). Fractions homogenous in the required product were combined, evaporated and the residual solid triturated with a mixture of pentane and ether affording the title compound (0.8 g) as a colourless solid, m.p. 104–108° C.

REFERENCE EXAMPLE 35

Methyl (RS)-(2-chlorophenyl)-[2-cyano-5-(pyridazin-4-ylmethoxy)phenoxy]acetate A stirred mixture of Reference Example 6 (0.481 g) and 4-chloromethylpyridazine hydrochloride (0.25 g) in dimethylformamide (6 ml) at 5° C. was treated with sodium hydride (0.121 g; 60% dispersion in mineral oil). After stirring at 5° C. for 1 hour the reaction mixture was allowed to warm to room temperature, stirring was continued for a further 2 hours at room temperature then at 60° C. for 4 hours. The reaction mixture was evaporated and the residual oil partitioned between ethyl acetate (50 ml) and water (20 ml). The aqueous phase was extracted three times with ethyl acetate. The combined organic phases were washed with brine (5 ml), dried over magnesium sulphate and evaporated. The residual oil (700 mg) was purified by flash chromatography on silica eluting with a mixture of dichloromethane and methanol (99:1, v/v). Fractions homogenous in the required product were combined and evaporated affording the title compound (0.2 g) as a white solid, m.p. 136–138° C. [Elemental analysis:-C,61.45; H,3.92; N,10.11%. Calculated:-C,61.54; H,3.93; N,10.25%].

REFERENCE EXAMPLE 36

4-(1,3-Benzodioxol-5-ylmethoxy)-2-fluorobenzonitrile

A mixture of 2-fluoro-4-hydroxybenzonitrile (S. M. Kelly, Helv.Chim.Acta. 1984, Volume 67, P.1572–1579) (30 g), potassium carbonate (45.36 g) and 3,4-methylenedioxybenzyl chloride (42.65 g) in dimethylformamide (500 ml) was stirred at 90° C. for 2 hours. The reaction mixture was filtered and the filtrate evaporated. The residue was stirred with ethyl acetate (500 ml) and filtered affording the title compound (32.1 g) as a cream coloured solid, m.p. 139–140° C.

REFERENCE EXAMPLE 37

Methyl (RS)-(2-chlorophenyl)-[2-cyano-5-(isothiazol-4-ylmethoxy)phenoxy]acetate A stirred solution of triphenylphosphine (2.2 g) in tetrahydrofuran at −5° C. was treated dropwise with diisopropyl azodicarboxylate (1.65 ml). After stirring −5° C. for 30 minutes a solution of Reference Example 6 (1.5 g) in dry tetrahydrofuran (5 ml) was added, followed by a solution of 4-hydroxymethylisothiazole (0.5 g) resulting in the formation of a red solution. The reaction mixture was allowed to warm to room temperature, then stood at room temperature for 18 hours and evaporated. The residue was treated with ethyl acetate (40 ml) and the organic phase washed twice with water (20 ml), then with brine (20 ml), dried over magnesium sulphate and evaporated. The residual amber coloured oil (7 g) was purified by flash chromatography on silica eluting with a mixture of ether and pentane (1:1, v/v). Fractions homogenous in the required product were combined and evaporated. The resulting yellow gum (1.44 g) was triturated with ether (25 ml) affording the title compound (0.44 g) as a white solid.

REFERENCE EXAMPLE 38

Methyl (RS)-[2-cyano-5-(3-pyridylmethoxy) phenoxy]-phenylacetate

A mixture of Reference Example 41 (0.5 g), methyl (RS)-a-bromophenylacetate (0.55 g) and potassium carbonate (0.5 g) in dimethylformamide (25 ml) was stirred at ambient temperature for 1.5 hours. The reaction mixture was diluted with water, the pH of the solution adjusted to 4–5 by addition of 2 N hydrochloric acid and the mixture extracted with ethyl acetate. The organic extracts were washed with brine, dried over magnesium sulphate and evaporated. The residual oil was purified by flash chromatography on silica eluting with a mixture of pentane and ethyl acetate (3:1, v/v). Fractions homogenous in the required product were combined and evaporated affording the title compound (0.52 g) as a white solid.

REFERENCE EXAMPLE 39

2-Hydroxy-4-(3-pyridylmethoxy)benzaldehyde

A mixture of 2,4-dihydroxybenzaldehyde (25 g), 3-picolyl chloride hydrochloride (38.2 g), potassium carbonate (91 g), potassium iodide (0.5 g) and tetra-n-butylammonium bromide (0.5 g) in methyl ethyl ketone (1000 ml) was heated at reflux for 4 hours. The reaction mixture was filtered and evaporated. The residue was partitioned between ethyl acetate and dilute acetic acid. The organic phase was washed with water, dried over magnesium sulphate and evaporated. The residue was purified by flash chromatography on silica eluting initially with a mixture of pentane and ethyl acetate (3:1, v/v) then with a mixture of pentane and ethyl acetate (1:1, v/v) and finally with a mixture of pentane and ethyl acetate (85:15, v/v). Fractions homogenous in the required product were combined and evaporated affording the title compound (5 g) as an off-white solid.

REFERENCE EXAMPLE 40

2-Hydroxy-4-(3-pyridylmethoxy)benzaldehyde Oxime

A mixture of Reference Example 39 (5 g), hydroxylamine hydrochloride (1.72 g) and pyridine (2 ml) in ethanol (100 ml) was heated at reflux for 1.5 hours. The reaction mixture was evaporated and the residual solid triturated with diethyl ether affording the title compound (2.7 g).

REFERENCE EXAMPLE 41

2-Hydroxy-4-(3-pyridylmethoxy)benzonitrile

A mixture of Reference Example 40 (2.5 g), sodium acetate (0.03 g) and acetic anhydride (10 ml) was heated at reflux for 1.5 hours. The cooled reaction mixture was carefully diluted with water (250 ml) with stirring and filtered. The resulting brown oil was extracted with ethyl acetate. Evaporation of the organic extracts and crystallisation from isopropanol afforded 2-acetoxy-4-(3-pyridylmethoxy)benzonitrile (2.15 g) which was dissolved in a mixture of methanol (10 ml) and tetrahydrofuran (7.5 ml) and treated, at room temperature, with a solution of potassium carbonate (1 g) in water (10 ml). After 2 hours the reaction mixture was diluted with water (50 ml) and the pH of the mixture was adjusted to 4 by addition of 2 N hydrochloric acid. The mixture was extracted with ethyl acetate. The organic extracts were washed with brine, dried over magnesium sulphate and evaporated affording the title compound (1.12 g) as a white solid.

REFERENCE EXAMPLE 42

Methyl (RS)-[2-formyl-5-(3-thienylmethoxy)phenoxy]-phenylacetate

A mixture of Reference Example 24 (3.00 g), methyl (RS)-α-bromophenylacetate (3.23 g) and potassium carbonate (2.65 g) in dimethylformamide (50 ml) was stirred at 25° C. for 1.5 hours. The reaction mixture was treated with water (50 ml), acidified to pH 3 by addition of concentrated hydrochloric acid and extracted five times with ethyl acetate (100 ml). The combined extracts were washed with brine (100 ml), dried and evaporated. The residual cream solid was washed with diethyl ether affording the title compound (2.80 g) as a white solid.

REFERENCE EXAMPLE 43

Methyl (RS)-(2-chlorophenyl)-[2-cyano-3-fluoro-5-(3-thienylmethoxy)phenoxy]acetate A solution of Reference Example 44 (0.97 g) in dry tetrahydrofuran (40 ml) was treated with sodium hydride (0.17 g, 60% dispersion in mineral oil). After stirring at room temperature for 30 minutes the reaction mixture was treated with a solution of Reference Example 10 (1.12 g) in dry dimethylformamide (10 ml) and stirring was continued at ambient temperature for 2 hours. The reaction mixture was diluted with water (100 ml), the pH of the solution was adjusted to 3 by addition of 1 N hydrochloric acid and extracted four times with ethyl acetate (50 ml). The combined organic extracts were washed with brine (50 ml), dried over magnesium sulphate and evaporated. The residual dark yellow oil was purified by flash chromatography on silica eluting with a mixture of light petroleum and ethyl acetate (4:1, v/v). Fractions homogenous in the required product were combined and evaporated affording the title compound (0.95 g) as a white solid, m.p. 143–144° C.

REFERENCE EXAMPLE 44

2-Fluoro-6-hydroxy-4-(3-thienylmethoxy)benzonitrile

A mixture of Reference Example 45 (1 g), nitroethane (0.6 g), sodium acetate (0.66 g) and glacial acetic acid (1 ml) was heated at reflux for 2 hours. The reaction mixture was cooled to ambient temperature, water (50 ml) was added and the mixture extracted three times with ethyl acetate (50 ml). The combined organic extracts were washed with saturated brine (50 ml), dried over magnesium sulphate and evaporated. The residual brown oil was purified by flash chromatography on silica eluting with a mixture of ethyl acetate and pentane (1:2, v/v). Fractions homogeneous in the required product were combined and evaporated to give the title compound (250 mg) as a yellow solid.

REFERENCE EXAMPLE 45

2-Fluoro-6-hydroxy-4-(3-thienylmethoxy)benzaldehyde

Sodium hydride (0.52 g, 60% dispersion in mineral oil) was added portionwise over 30 minutes to a solution of Reference Example 46 (2 g) in dimethylformamide (50 ml) at 0° C. After stirring at 0° C. for 30 minutes a solution of 3-chloromethylthiophene (1.72 g) in dimethylformamide (50 ml) was added and the mixture stirred at 60° C. for 16 hours. The reaction mixture was concentrated and the residue partitioned between diethyl ether (50 ml) and water (50 ml). The aqueous phase was extracted four times with diethyl ether (50 ml) and the combined organic extracts washed with brine (50 ml), dried over magnesium sulphate and evaporated. The residue was purified by flash chromatography on silica eluting with a mixture of ethyl acetate and pentane (1:4, v/v). Fractions homogeneous in the required product were combined and evaporated to give a pale yellow solid which was triturated with diisopropyl ether to give the title compound (1.1 g) as a yellow solid.

REFERENCE EXAMPLE 46

2,4-Dihydroxy-6-fluorobenzaldehyde

Dimethylformamide (12.7 g) was added to vigorously stirred phosphorous oxychloride (14.4 g) at 0° C. The reaction mixture was stirred at this temperature for 30 minutes, then 3,5-dihydroxyfluorobenzene (6 g) was added. The sticky red syrup was allowed to warm to room temperature and stirred for 2 hours, then left to stand for 14 hours. Water (100 ml) was added and the mixture extracted three times with ethyl acetate (100 ml). The combined organic extracts were washed with brine (100 ml), dried over magnesium sulphate and evaporated. The residue was purified by flash chromatography on silica eluting with a mixture of ethyl acetate and pentane (1:2, v/v). Fractions homogeneous in the required product were combined and evaporated to give an orange solid which was triturated with ethyl acetate to give the title compound (2 g) as a yellow solid.

REFERENCE EXAMPLE 47

Methyl (RS)-[5-(benzoxazol-6-ylmethoxy)-2-cyanophenoxy]-(2-chlorophenyl)acetate

A mixture of Reference Example 6 (3.24 g), Reference Example 48 (2.17 g) and potassium carbonate (1.41 g) in dry dimethylformamide (60 ml) was stirred at room temperature under nitrogen for 18 hours. The reaction mixture was evaporated, water (60 ml) was added and the solution extracted three times with ethyl acetate (60 ml). The combined extracts were washed twice with water (40 ml), with brine (50 ml), dried over magnesium sulphate and evaporated. The residual material was purified by flash chromatography on silica eluting with a mixture of diethyl ether and pentane (1:1, v/v). Fractions homogenous in the required product were combined and evaporated. The residue was triturated twice with pentane (10 ml) affording the title compound (1.49 g) as a white solid, m.p. 157–159° C. [Elemental analysis:-C,64.9; H,3.96; N,6.33; Cl,7.77%. Calculated:-C,64.22; H,3.82; N,6.24; Cl,7.89%].

REFERENCE EXAMPLE 48

6-Bromomethylbenzoxazole

A mixture of 6-methylbenzoxazole (5.0 g; J. T. Gupton, K. F. Correia and B. S. Foster, Synthetic Communications, 1986, 16, 365), N-bromosuccinimide (7.0 g) and azobisisobutyronitrile (0.55 g) in dry chloroform (100 ml) was heated at reflux for 1 hour. The cooled reaction mixture was washed three times with water (40 ml), dried over magnesium sulphate and evaporated. The residual orange coloured viscous solid was triturated twice with pentane (50 ml) affording the title compound (6.20 g) as a buff coloured solid, m.p. 52–56° C.

REFERENCE EXAMPLE 49

Ethyl (RS)-α-hydroxy-[2-(3-methyl)thienyl]acetate

A stirred solution of ethyl 2-[2-(3-methyl)thienyl]-2-oxoacetate (5.5 g) in tetrahydrofuran (50 ml) and water (2 ml) was cooled in an acetone/ice bath and treated with sodium borohydride (0.45 g). After stirring in the ice bath for about 1 hour a little acetone was added to destroy excess borohydride, and the mixture evaporated to low bulk. The residue was partitioned between ethyl acetate and 0.1 N hydrochloric acid. The organic phase was washed with 5% aqueous sodium bicarbonate solution, then with water, dried over magnesium sulphate and evaporated. The residue was purified by passage down a short bed of silica, eluting initially with a mixture of dichloromethane and cyclohexane (1:1, v/v) then with dichloromethane. Fractions homogenous in the required product were combined and evaporated affording the title compound (1.14 g) as a colourless mobile oil.

REFERENCE EXAMPLE 50

2-Fluoro-4-(thiazol-5-ylmethoxy)benzonitrile

Diisopropylazodicarboxylate (4.0 g) was dissolved in a little anhydrous tetrahydrofuran (about 10 ml) and added dropwise to a stirred solution of triphenylphosphine (5.2 g) in anhydrous tetrahydrofuran (150 ml) at 0° C. under nitrogen. After stirring at 0 C. for 15 minutes, during which time a white precipitate formed, a mixture of 2-fluoro-4-hydroxybenzonitrile (S. M. Kelly, Helv.Chim.Acta. 1984, Volume 67, P.1572–1579) (2.0 g) and thiazole-5-methanol (2.3 g) in anhydrous tetrahydrofuran (20 ml) was added dropwise whilst maintaining the temperature at or below 5° C. The reaction mixture was stirred in the cooling bath for a further 2 hours then allowed to warm slowly to room temperature. After standing at room temperature overnight the reaction mixture was partitioned between ethyl acetate (200 ml) and saturated aqueous ammonium chloride solution (200 ml). The layers were separated and the organic phase washed with water (100 ml), dried over magnesium sulphate and evaporated. The residue was purified by flash chromatography on silica eluting with a mixture of ethyl acetate and cyclohexane (1:1, v/v). Fractions homogenous in the required product were combined and evaporated affording the title compound as a pale yellow solid (2.0 g).

REFERENCE EXAMPLE 51

Methyl (RS)-(2-chlorophenyl)-[2-cyano-3-fluoro-5-(4-pyridylmethoxy)phenoxy]acetate A mixture of Reference Example 52 (0.6 g), 4-picolylchloride hydrochloride (0.32 g), potassium carbonate (1.24 g), potassium iodide ((0.15 g) and tetra-n-butylammonium bromide (20 mg) in methyl ethyl ketone (30 ml) was heated to reflux and maintained for 1 hour. The mixture was evaporated to dryness and partitioned between 10% acetic acid (50 ml) and ethyl acetate (50 ml). The organic layer was separated and the aqueous layer extracted twice with ethyl acetate (250 ml). The combined organic extracts were washed with saturated brine (50 ml), dried over magnesium sulphate and evaporated affording the title compound (0.72 g) as a brown oil, which was used without further purification.

REFERENCE EXAMPLE 52

Methyl (RS)-(2-chlorophenyl)-[2-cyano-3-fluoro-5-hydroxyphenoxy]acetate

Nitrogen was bubbled through a solution of Reference Example 53 (0.66 g) in ethanol (60 ml) and water (6 ml) for 20 minutes. Diazabicyclo[2,2,2]octane (0.04 g) and tris (triphenylphosphine)rhodium (I) chloride (0.125 g) were added and the mixture heated to reflux. After refluxing for 4.5 hours the reaction mixture was cooled to room temperature and partitioned between 1 N hydrochloric acid (50 ml) and ethyl acetate (50 ml). The organic layer was separated and the aqueous layer extracted twice with ethyl acetate (50 ml). The combined organic extracts were washed with saturated brine (50 ml), dried over magnesium sulphate and evaporated. The residual yellow oil was purified by flash chromatography on silica eluting with a mixture of ethyl acetate and petroleum ether (33:67, v/v). Fractions homogenous in the required product were combined and evaporated affording the title compound (0.6 g) as a yellow oil.

REFERENCE EXAMPLE 53

Methyl (RS)-[5-allyloxy-2-cyano-3-fluorophenoxy]-(2-chlorophenyl)acetate

A solution of Reference Example 54 (0.52 g) in dry dimethylformamide (30 ml) under nitrogen was treated with sodium hydride (0.12 g, 60% dispersion in mineral oil). The mixture was stirred at room temperature for 20 minutes then treated dropwise with a solution of Reference Example 10 (0.78 g) in dry dimethylformamide (10 ml). The resulting solution was stirred at room temperature for 1 hour, quenched with water (50 ml), the solution acidified to pH 1 by addition of 1 N hydrochloric acid and extracted four times with diethyl ether (40 ml). The combined organic extracts were washed with saturated brine (50 ml), dried over magnesium sulphate and evaporated. The residual red oil was purified by flash chromatography on silica eluting with a mixture of ethyl acetate and petroleum ether (1:5, v/v). Fractions homogenous in the required product were combined and evaporated affording the title compound (1.01 g) as a colourless foam.

REFERENCE EXAMPLE 54

4-Allyloxy-2-fluoro-6-hydroxybenzonitrile

A mixture of Reference Example 55 (1.1 g) in methanol (20 ml) and 10% potassium carbonate solution (13.5 ml) was stirred at room temperature for 30 minutes then evaporated to low bulk. The residue was partitioned between water (50 ml) and pentane (50 ml). The aqueous layer was acidified to pH 1 by addition of 1 N hydrochloric acid and extracted three times with diethyl ether (40 ml). The combined organic extracts were washed with saturated brine (50 ml), dried over magnesium sulphate and evaporated. The residual pale pink solid was triturated with pentane affording the tite compound (0.87 g) as a pale pink solid, m.p. 153–155° C.

REFERENCE EXAMPLE 55

2-Acetoxy-4-allyloxy-6-fluorobenzonitrile

A mixture of Reference Example 56 (0.96 g), sodium acetate (20 mg) and acetic anhydride was heated at reflux for 1.5 hours. The reaction mixture was allowed to cool to room temperature, diluted with water (50 ml) and extracted four times with diethyl ether (30 ml). The combined organic extracts were washed with saturated brine (50 ml), dried over magnesium sulphate and evaporated affording the title compound (1.13 g) as a red/pink oil which was used without further purification.

REFERENCE EXAMPLE 56

4-Allyloxy-2-fluoro-6-hydroxybenzaldoxime

A mixture of Reference Example 57 (0.92 g), hydroxylamine hydrochloride (0.33 g) and pyridine (0.37 g) in ethanol (50 ml) was stirred at reflux for 1 hour. The mixture was cooled to room temperature and concentrated to low volume and partitioned between water (50 ml) and diethyl ether (50 ml). The aqueous layer was extracted twice with diethyl ether (50 ml). The combined organic extracts were washed with saturated brine (50 ml), dried over magnesium sulphate and evaporated affording the title compound as a pink oil (0.99 g), which was used without further purification.

REFERENCE EXAMPLE 57

4-Allyloxy-2-fluoro-6-hydroxybenzaldehyde

A mixture of Reference Example 46 (2 g), allyl bromide (0.78 g), potassium carbonate (0.97 g) and potassium iodide (0.14 g) in methyl ethyl ketone (100 ml) was heated at reflux for 2 hours. The reaction mixture was poured into water (200 ml) and extracted three times with diethyl ether (100 ml). The combined organic extracts were washed with saturated brine (200 ml), dried over magnesium sulphate and evaporated. The residual brown oil was purified by flash chromatography on silica eluting with a mixture of ethyl acetate and pentane (12:88, v/v). Fractions homogenous in the required product were combined and evaporated affording the title compound (0.92 g) as a pale yellow oil.

REFERENCE EXAMPLE 58

(RS)-(2-Chlorophenyl)-(1H-tetrazol-5-yl)methanol

A stirred solution of Reference Example 59 (4.26 g) in acetonitrile (400 ml) and water (50 ml) at 5° C. was treated with ammonium cerium (IV) nitrate (35 g) over 10 minutes. The reaction mixture was allowed to warm to ambient temperature and stirring was continued for 5 hours. The reaction mixture was diluted with dichloromethane (800 ml) and washed with water (600 ml). The organic phase was dried over magnesium sulphate, evaporated and the residue purified by flash chromatography on silica eluting with a mixture of ethyl acetate and pentane (1:1, v/v). Fractions homogenous in the required product were combined and evaporated affording the title compound (1.33 g) as a solid, m.p. 130–132° C. [Elemental analysis:-C,45.93; H,3.35; N,26.0%. Calculated:-C,45.62; H,3.35; N,26.6%].

REFERENCE EXAMPLE 59

(RS)-(2-Chlorophenyl)-[1-(4-methoxybenzyl)-1H-tetrazol-5-yl]methanol

A solution of 1-(4-methoxybenzyl)tetrazole (6.12 g; Y. Satoh and N. Marcopulos, Tetrahedron Letters, 1995, 36, 1759–1762), and N,N,N'N'-tetramethylethylenediamine (10 ml) in dry tetrahydrofuran (10 ml) under nitrogen was cooled to −95° C. and treated dropwise with n-butyl lithium (2.5 M solution in hexanes) over 15 minutes. The reaction mixture was left at −80° C. for 15 minutes when 2-chlorobenzaldehyde (4.53 g) was added dropwise over 10 minutes maintaining the reaction temperature at or below −80° C. The mixture was stirred at or below −80° C. for 30 minutes, allowed to warm to room temperature, quenched with ammonium chloride solution (50 ml) and the organic phase separated. The aqueous phase was extracted three times with ethyl acetate (50 ml), the combined organics dried over magnesium sulphate and evaporated. The residue was purified by flash chromatography on silica eluting initially with a mixture of ethyl acetate and pentane (1:1, v/v) then with a mixture of ethyl acetate and pentane (2:1, v/v). Fractions homogenous in the required product were combined and evaporated affording the title compound (1.33 g) as a white solid, m.p. 128–130° C. [Elemental analysis:-C,58.22; H,4.74; N,17.15%. Calculated:-C,58.1; H,4.57; N,16.94%].

REFERENCE EXAMPLE 60

Methyl (RS)[3-chloro-2-cyano-5-(4-pyridylmethoxy)phenoxy]-(2-chlorophenyl)acetate A mixture of Reference Example 61 (0.15 g), 4-picolylchloride hydrochloride (0.15 g), potassium carbonate (0.59 g), potassium iodide (70 mg) and tetra-n-butylammonium bromide (10 mg) in methyl ethyl ketone (20 ml) was heated at reflux for 1 hour. The reaction mixture was evaporated and partitioned between 10% acetic acid (30 ml) and ethyl acetate (30 ml). The organic layer was separated and the aqueous layer extracted twice with ethyl acetate (30 ml). The combined organic extracts were washed with saturated brine (30 ml), dried over magnesium sulphate and evaporated affording the title compound as a pale green gum (0.3 g), which was used without further purification.

REFERENCE EXAMPLE 61

Methyl (RS)[3-chloro-2-cyano-5-hydroxyphenoxy]-(2-chlorophenyl)acetate

Nitrogen was bubbled through a solution of Reference Example 62 (0.66 g) in ethanol (20 ml) and water (2 ml) for 20 minutes. Diazobicyclo[2,2,2]octane (0.021 g) and tris(triphenylphosphine)rhodium(I) chloride (61 mg) were added and the mixture heated to reflux for 2 hours. The reaction mixture was partitioned between 1 N hydrochloric acid (40 ml) and ethyl acetate (40 ml). The organic layer was separated and the aqueous layer extracted twice with ethyl acetate (40 ml). The combined organic extracts were washed with saturated brine (40 ml), dried over magnesium sulphate and evaporated. The residual yellow oil was purified by flash chromatography on silica eluting with a mixture of ethyl acetate and petroleum ether (33:67, v/v). Fractions homogenous in the required product were combined and evaporated affording the title compound (0.3 g) as a colourless oil.

REFERENCE EXAMPLE 62

Methyl (RS)-[5-allyloxy-3-chloro-2-cyanophenoxy]-(2-chlorophenyl)acetate

To a solution of Reference Example 63 (0.37 g) in dry dimethylformamide (20 ml) under a nitrogen atmosphere was added sodium hydride (0.76 g, 60% dispersion in mineral oil). The mixture was stirred at room temperature for 20 minutes then treated dropwise with a solution of Reference Example 10 (0.51 g) in dry dimethylformamide (5 ml). The resulting solution was stirred at room temperature for 1 hour, diluted with water (50 ml), acidified to pH 1 by addition of 1 N hydrochloric acid and extracted three times with diethyl ether (40 ml). The combined organic extracts were washed with saturated brine (40 ml), dried over magnesium sulphate and evaporated. The residual yellow oil was purified by flash chromatography on silica eluting with a mixture of ethyl acetate and petroleum ether (1:4, v/v). Fractions homogenous in the required product were combined and evaporated affording the title compound (0.36 g) as a white solid.

REFERENCE EXAMPLE 63

4-Allyloxy-2-chloro-6-hydroxybenzonitrile

A solution of Reference Example 64 (0.63 g) in methanol (20 ml) and 10% potassium carbonate solution (3 ml) was stirred at room temperature for 30 minutes and evaporated to low bulk. The residue was partitioned between water (50 ml) and diethyl ether (30 ml). The organic layer was separated and discarded. The aqueous layer was acidified to pH 1 by addition of 1 N hydrochloric acid and extracted three times with diethyl ether (40 ml). The combined organic extracts were washed with saturated brine (30 ml), dried over magnesium sulphate and evaporated affording the title compound (0.37 g) as a white solid, m.p. 175–176° C.

REFERENCE EXAMPLE 64

2-Acetoxy-4-allyloxy-6-chlorobenzonitrile

A mixture of Reference Example 65 (0.63 g), sodium acetate (20 mg) and acetic anhydride was heated at reflux for 1.5 hours. The reaction mixture was diluted with water (50 ml) and extracted four times with diethyl ether (30 ml). The combined organic extracts were washed three times with saturated sodium hydrogen carbonate solution (40 ml), with saturated brine (50 ml), dried over magnesium sulphate and evaporated affording the title compound as a yellow/brown gum (0.75 g) which was used without further purification.

REFERENCE EXAMPLE 65

4-Allyloxy-2-chloro-6-hydroxybenzaldehyde Oxime

A mixture of Reference Example 66 (0.53 g), hydroxylamine hydrochloride (0.17 g), pyridine (0.2 g) and ethanol (30 ml) was stirred at reflux for 1 hour. The mixture was concentrated to low volume and partitioned between water (50 ml) and diethyl ether (50 ml). The aqueous layer was separated and extracted twice with diethyl ether (50 ml). The combined organic extracts were washed with saturated brine (50 ml), dried over magnesium sulphate and evaporated affording the title compound as a white solid (0.63 g), m.p. 65–66° C., which was used without further purification.

REFERENCE EXAMPLE 66

4-Allyloxy-2-chloro-6-hydroxybenzaldehyde

A mixture of Reference Example 67 (3.7 g), allyl bromide (1.3 g), potassium carbonate (1.5 g) and potassium iodide (200 mg) in methyl ethyl ketone (100 ml) was heated at reflux for 2 hours. The reaction mixture was poured into water (200 ml) and extracted three times with diethyl ether (100 ml). The combined organic extracts were washed with saturated brine (200 ml) and dried over magnesium sulphate and evaporated. The residual brown oil was purified by flash chromatography on silica eluting with a mixture of ethyl acetate and petroleum ether (1:8, v/v). Fractions homogenous in the required product were combined and evaporated affording the title compound (0.53 g) as a pale yellow crystalline solid m.p. 35–36° C.

REFERENCE EXAMPLE 67

2-Chloro-4,6-dihydroxybenzaldehyde

Pyrophosphonyl chloride (19.49 g) was added dropwise to dimethylformamide (10.84 ml) over 20 minutes, keeping the temperature at 5° C. To the viscous mixture was added a solution of Reference Example 68 (10.17 g) in dimethylformamide (5 ml). The mixture was vigorously stirred at room temperature for 7 hours, and left to stand for another 18 hours. The reaction mixture was neutralised with saturated sodium acetate solution (1000 ml) and was then extracted three times with ethyl acetate (400 ml). The combined organic extracts were washed with saturated brine (300 ml), dried over magnesium sulphate and evaporated.

The residual orange oil was purified by flash chromatography on silica eluting with a mixture of methanol and dichloromethane (2:98, v/v). Fractions homogenous in the required product were combined and evaporated affording the title compound (3.7 g) as a yellow oil.

REFERENCE EXAMPLE 68

5-Chloro-1,3-Dihydroxybenzene

A solution 5-chloro-1,3-dimethoxybenzene (20.71 g) in dichloromethane (50 ml) at −78° C. was treated dropwise with a solution of boron tribromide (56 ml) in dichloromethane (250 ml), maintaining the temperature at −78° C. The mixture was slowly warmed to room temperature then left at ambient temperature for 48 hours. The reaction mixture was quenched with water (100 ml), (sodium hydroxide scrubber required) and partitioned between water (1000 ml) and dichloromethane (1000 ml). The organic layer was separated and the aqueous layer was extracted twice with a mixture of dichlioromethane and methanol (500 min, 98:2, v/v). The combined organic extracts were washed with saturated brine (200 ml), dried over magnesium sulphate and evaporated affording the title compound (10.17 g) as a yellow/orange oil which was used without further purification.

REFERENCE EXAMPLE 69

Methyl (RS)-[5-(benzoxazol-6-ylmethoxy)-2-cyanophenoxy]-(2-methylphenyl)acetate

A mixture of Reference Example 70 (3.24 g), Reference Example 48 (2.17 g) and potassium carbonate (1.41 g) in dry dimethylformamide (60 ml) was stirred at room temperature under nitrogen for 18 hours. The reaction mixture was evaporated, water (60 ml) was added and the solution extracted three times with ethyl acetate (60 ml). The combined extracts were washed twice with water (40 ml), then with brine (50 ml), dried over magnesium sulphate and evaporated. The residual material was purified by flash chromatography on silica eluting with a mixture of diethyl ether and pentane (1:1, v/v). Fractions homogenous in the required product were combined and evaporated. The residual solid was triturated twice with pentane (10 ml) affording the title compound (1.49 g) as a white solid, m.p. 157–159° C. [Elemental analysis:-C,64.9; H,3.96; N,6.33; Cl,7.77%. Calculated:-C,64.22; H,3.82; N,6.24; Cl,7.89 %].

REFERENCE EXAMPLE 70

Methyl (RS)-(2-cyano-5-hydroxyphenoxy)-(2-methylphenyl)acetate

A stirred solution of Reference Example 71 (17.9 g) in methanol (700 ml) was treated with 1,4-diazabicyclo(2.2.2) octane (11.9 g) and tris(triphenylphosphine)rhodium(I) chloride (2.45 g) and refluxed for 1 hour. The reaction mixture was evaporated and the residue treated with 2 N hydrochloric acid (400 ml). This mixture was extracted four times with ethyl acetate (200 ml). The combined extracts were washed with water, then with brine, dried over magnesium sulphate and evaporated. The residual oil was purified by flash chromatography on silica eluting with a mixture of ethyl acetate and pentane (1/1, v/v). Fractions homogenous in the required product were evaporated. The residue was triturated with pentane affording the title compound (9.5 g) as a colourless solid, m.p. 114–121° C. [Elemental analysis:-C,68.7; H,5.06; N,4.51%. Calculated:-C,68.7; H,5.09; N,4.71%].

REFERENCE EXAMPLE 71

Methyl (RS)-(5-allyloxy-2-cyanophenoxy)-(2-methylphenyl)acetate

A stirred solution of Reference Example 4 (35.0 g) in dry dimethylformamide (350 ml) was treated portionwise with sodium hydride (8.0 g, 60% dispersion in mineral oil). After stirring at ambient temperature for 30 minutes the mixture was treated with Reference Example 21 (48.6 g) and stirring was continued for 24 hours. The reaction mixture was evaporated (45° C./0.1 mm) and the residue treated with water (250 ml) and extracted three times with ethyl acetate (250 ml). The combined extracts were washed with water, dried over magnesium sulphate and evaporated. The residual oil was purified by flash chromatography on silica eluting with dichloromethane. Fractions homogenous in the required product were combined and evaporated. The residue was triturated with pentane affording the title compound (46.6 g) as a colourless solid, m.p. 98–99° C. [Elemental analysis:-C,71.2; H,5.71; N,4.07%. Calculated:-C,71.2; H,5.68; N,4.15%].

REFERENCE EXAMPLE 72

(a)(S)-[5-(1,3-Benzodioxol-5-ylmethoxy)-2-cyanophenoxy]-(2-methylphenyl)acetic acid, (−) Ephedrine Salt Method A: A solution of Example 19 (0.5 g) in diethyl ether (5 ml) was treated with a solution of (−) ephedrine (0.2 g) in diethyl ether (10 ml). After stirring at ambient temperature for 30 minutes the mixture was evaporated and the residue recrystallized twice from a mixture of ethyl acetate and pentane affording the title compound (0.15 g, ee 99.7%) as a white solid, m.p. 171–173° C. [Elemental analysis:-C, 69.92; H,5.89; N,4.87%. Calculated:-C,70.09; H,5.88; N,4.81%].

Method B: Reference Example 87 (30.0 g, 73%ee) was added portionwise (ca 2.5 g every 15 minutes) over 3 hours to a stirred, thick white slurry of Reference Example 15 (18.62 g) and powdered potassium phosphate (73.42 g) in methyl ethyl ketone (200 ml) at about 18° C. The reaction mixture was stirred at ambient temperature (about 22° C.) for 2.5 hours. Demineralized water (125 ml) was added and the pH of the mixture was adjusted to 7–7.5 by addition of hydrochloric acid (s.g. 1.18, about 35 ml). The aqueous layer was removed then fresh demineralized water (150 ml) was added and volatile organics were removed by distillation until the distillate temperature reached 80° C. Ethanol (15 ml) was added and distillation was continued until a further 15 ml of distillate had been collected. The residue was heated and ethanol (95 ml) was added slowly to bring the reaction mixture to a homogeneous boiling solution, which was then stirred slowly while being allowed to cool. At 55° C. seed crystals of the product were added and cooling was gradually continued to 50° C. The product was collected by filtration then washed by resuspending twice in demineralized water (100 ml) and dried by suction. The product was suspended in a mixture of ethyl acetate (74 ml) and tert-butyl methyl ether (222 ml). The mixture was heated under reflux with Dean and Stark azeotropic removal of water for at least 5 hours. The slurry was cooled to about 20° C. and filtered. The product was washed with tert-butyl methyl ether (20 ml) then dried at about 50° C. to give the title compound (21.3 g, ee 97.2%).

Method C: A solution of potassium tert-butoxide (137.5 g) in tetrahydrofuran (500 ml) was added dropwise, over 1 hour, to a stirred suspension of Reference Example 87 (207.1 g, ee 78%) and Reference Example 15 (94.27 g) in tetrahydrofuran (950 ml) maintaining the temperature between 16° C. and 19° C. The reaction mixture was then stirred at ambient temperature (ca. 22° C.) for 1.5 hours. Demineralized water (1050 ml) was added over 5 minutes. The pH of the resulting solution was adjusted to 7–7.5 by addition of hydrochloric acid (s.g. 1.18). The mixture was concentrated by distillation until the temperature of the distillate reached about 92° C., then ethanol (200 ml) was added. Distillation was continued until the distillate reached about 91° C. Ethanol (600 ml) was added to the hot mixture over about 10 minutes to bring the reaction mixture to a homogeneous boiling solution. Heating was discontinued and the solution was stirred slowly while being allowed to cool to 20° C. The product was filtered, washed by being resuspended twice in demineralized water (500 ml) and dried by suction. The product was then suspended in a mixture of ethyl acetate (375 ml) and tert-butyl methyl ether (1125 ml). The mixture was heated under reflux with Dean and Stark azeotropic removal of water for at least 5 hours. The slurry was cooled to about 200° C. and filtered. The product was washed with tert-butyl methyl ether (100 ml) then dried at about 50° C. to give the title compound (107.7 g; ee 97.2%).

(b) In a similar manner to method A but replacing Example 19 with Example 42 may be prepared (S)-[5-(1,3-Benzodioxol-5-ylmethoxy)-2-cyano-3-fluorophenoxy]-(2-methylphenyl)acetic acid, (–) ephedrine salt.

REFERENCE EXAMPLE 73

Methyl (RS)-[5-(1,3-benzodioxol-5-ylmethoxy)-2-cyanophenoxy]-(2-methylphenyl)acetate Method A: A mixture of Reference Example 70 (120 g), 3,4-methylenedioxybenzyl chloride (82.4 g) and potassium carbonate (83.8 g) in dimethylformamide (650 ml) was stirred at room temperature for 1.5 hours then at 50° C. for 1.5 hours. The reaction mixture was filtered and the filtrate evaporated. The residue was dissolved in ethyl acetate (500 ml), washed twice with 1 N sodium hydroxide (150 ml), then with brine (150 ml), dried over magnesium sulphate and evaporated. The residue was triturated with diethyl ether affording the title compound (135.5 g) as a cream coloured solid, m.p. 107–108° C.

Method B: A solution of Reference Example 15 (39.6 g) in dimethylformamide (500 ml) was treated with sodium hydride (6 g, 60% dispersion in mineral oil). After stirring at ambient temperature for 20 minutes the mixture was treated with a solution of Reference Example 21 (39.4 g) in dimethylformamide (50 ml) and stirring was continued for 3 hours. The reaction mixture was evaporated and partitioned between ethyl acetate (500 ml) and water (300 ml). The aqueous phase was extracted twice with ethyl acetate (200 ml) and the combined organic phases washed with brine (250 ml), dried over magnesium sulphate and evaporated. The residue was triturated with diethyl ether affording the title compound (57.4 g) as a white solid, m.p. 112–114° C.

REFERENCE EXAMPLE 74

Methyl (RS)-[2-cyano-5-(4-(3-fluoropyridyl)methoxy)phenoxy]-(2-methylphenyl)acetate A solution of Reference Example 70 (0.26 g) in dry dimethylformamide (5 ml) was treated with potassium carbonate (0.122 g) and the mixture stirred at room temperature for 15 minutes. A solution of Reference Example 75 (0.18 g) in dry dimethylformamide (1 ml) was added and stirring continued for 3 hours. The reaction mixture was diluted with water (100 ml) and extracted three times with ethyl acetate (20 ml). The combined extracts were washed with brine (25 ml), dried over magnesium sulphate and evaporated. The residual oil crystallised on standing at room temperature overnight. Trituration with a mixture of dichloromethane and ethyl acetate (4:1, v/v) afforded the title compound (0.05 g) as a white solid, m.p. 166–167° C. The soluble material was purified by flash chromatography on silica eluting with a mixture of dichloromethane and ethyl acetate (9:1, v/v). Fractions homogenous in the required product were combined and evaporated and the yellow oil triturated with pentane affording a further quantity of the title compound (0.1 g) as a white solid, m.p. 167–168° C.

REFERENCE EXAMPLE 75

4-Bromomethyl-2-fluoropyridine

A solution of 2-fluoro-4-methylpyridine (0.5 g) in chloroform (50 ml) was treated with N-bromosuccinimide (1.35 g) and azobisisobutyronitrile (0.25 g). The mixture was heated at reflux for 30 hours, cooled to room temperature and washed with water (30 ml). The chloroform solution was evaporated and the resulting brown oil purified by flash chromatography on silica eluting initially with a mixture of ethyl acetate and pentane (1:9, v/v) then with a mixture of ethyl acetate and pentane (15:85, v/v). Fractions homogenous in the required product were combined and evaporated affording the title compound (0.18 g) as a yellow oil.

REFERENCE EXAMPLE 76

(RS)-(2-Methylphenyl)-(1H-tetrazol-5-yl)methanol

A solution of Reference Example 77 (9.27 g) in acetonitrile (250 ml) and water (40 ml) cooled in an ice-bath was treated portionwise over 10 minutes with ammonium cerium (IV) nitrate (82.2 g). The reaction mixture was warmed to room temperature and stirred for 2.5 hours. The mixture was diluted with dichloromethane (800 ml) and washed with water (400 ml). The organic phase was dried over magnesium sulphate and evaporated. The residue was purified by flash chromatography on silica eluting with a mixture of ethyl acetate and pentane (1:1, v/v). Fractions homogenous in the required product were combined and evaporated affording the title compound (4.8 g) as a cream solid, m.p. 124–126° C.

REFERENCE EXAMPLE 77

(RS)-[1-(4-Methoxybenzyl)-1H-tetrazol-5-yl]-(2-methylphenyl)methanol

A stirred solution of 1-(4-methoxybenzyl)tetrazole (7.04 g, Tetrahedron Letters, 1995, p1759–1762) in a mixture of dry tetrahydrofuran (120 ml) and N,N,N',N',-tetramethylethylenediamine (12 ml) under a nitrogen atmosphere at –85° C. was treated dropwise with n-butyl lithium (18 ml, 2.5 M solution in hexanes) over 10 minutes. After stirring at –85° C. for an additional 5 minutes a solution of o-tolualdehyde (4.45 g) in dry tetrahydrofuran (20 ml) was added dropwise over 10 minutes. The reaction mixture was stirred at –85° C. for 30 minutes, allowed to warm to room temperature, then quenched with saturated ammonium chloride solution (50 ml). The organic phase was separated and the aqueous phase extracted three times with ethyl acetate (100 ml). The combined organic phases were dried over magnesium sulphate and evaporated. The residue was purified by flash chromatography on silica eluting initially with a mixture of ethyl acetate and pentane (1:1, v/v) then with a mixture of ethyl acetate and pentane (66:34, v/v). Fractions homogenous in the required product were combined and evaporated affording the title compound (9.8 g) as a whlite solid, m.p. 90–92° C. [Elemental analysis:-C,65.91, H,5.9, N,18.1%. Calculated:-C,65.79, H,5.85, N,18.05%].

REFERENCE EXAMPLE 78

Methyl (RS)-[2-cyano-3-fluoro-5-(4-pyridylmethoxy)phenoxy]-(2-methylphenyl)acetate A mixture of Reference Example 79 (0.5 g), 4-picolylchloride hydrochloride (0.29 g), potassium carbonate (1.11 g), potassium iodide (130 mg) and tetra-n-butylammonium bromide (20 mg) in methyl ethyl ketone (30 ml) was heated at reflux for 1 hour. The mixture was evaporated to dryness and partitioned between 10% acetic acid (50 ml) and ethyl acetate (50 ml). The organic phase was separated and the aqueous layer extracted twice with ethyl acetate (50 ml). The combined organic phases were washed with saturated brine (50 ml), dried over magnesium sulphate and evaporated affording the title compound (0.64 g) as a yellow oil, which was used without further purification.

REFERENCE EXAMPLE 79

Methyl (RS)-[2-cyano-3-fluoro-5-hydroxyphenoxy]-(2-methylphenyl)acetate

Nitrogen was bubbled through a solution of Reference Example 80 (3.1 g) in a mixture of ethanol (100 ml) and water (10 ml) for 20 minutes. The solution was treated with 1,4-diazabicyclo[2.2.2]octane (0.2 g) and tris(triphenylphosphine)rhodium(I) chloride (610 mg) and heated at reflux for 4.5 hours. The reaction mixture was cooled to room temperature and partitioned between 1 N hydrochloric acid (50 ml) and ethyl acetate (5 ml). The organic phase was separated and the aqueous layer extracted three times with ethyl acetate (50 ml). The combined organic phases were washed with saturated brine (50 ml), dried over magnesium sulphate and evaporated affording the title compound (3.7 g) as a yellow gum which was used without further purification.

REFERENCE EXAMPLE 80

Methyl (RS)-[5-allyloxy-2-cyano-3-fluorophenoxy]-(2-methylphenyl)acetate

A stirred solution of Reference Example 54 (3.0 g) in dry dimethylformamide (90 ml), under a nitrogen atmosphere was treated with sodium hydride (0.68 g, 60% dispersion in mineral oil). After stirring at ambient temperature for 20 minutes a solution of Reference Example 21 (4.15 g) in dry dimethylformamide (10 ml) was added dropwise. The resulting solution was stirred at room temperature for 3 hour then quenched with water (200 ml). The solution was acidified to pH 1 by addition of 1 N hydrochloric acid and extracted five times with diethyl ether (50 ml). The combined extracts were washed with saturated brine (50 ml), dried over magnesium sulphate and evaporated. The residual red oil was purified by flash chromatography on silica eluting with a mixture of ethyl acetate and petroleum ether (1:5, v/v). Fractions homogenous in the required product were combined and evaporated affording the title compound (3.1 g) as a white solid, m.p. 100–102° C.

REFERENCE EXAMPLE 81

Methyl (RS)-[5-(benzoxazol-6-ylmethoxy)-2-cyano-3-fluorophenoxy]-(2-methylphenyl)acetate A mixture of Reference Example 79 (0.5 g), Reference Example 48 (0.37 g), potassium carbonate (1.11 g), potassium iodide (130 mg) and tetra-n-butylammonium bromide (20 mg) in methyl ethyl ketone (30 ml) was heated at reflux for 1 hour. The reaction mixture was evaporated to dryness and partitioned between water (50 ml) and ethyl acetate (50 ml). The organic phase was separated and the aqueous layer extracted twice with ethyl acetate (50 ml). The combined organic extracts were washed with saturated brine (50 ml), dried over magnesium sulphate and evaporated. The residual colourless gum was purified by flash chromatography on silica eluting with a mixture of ethyl acetate and pentane (66:34, v/v). Fractions homogenous in the required product were combined and evaporated affording the title compound (0.35 g) as a colourless gum.

REFERENCE EXAMPLE 82

Methyl (RS)-[5-(1,3-benzodioxol-5-ylmethoxy)-2-cyano-3-fluorophenoxy]-(2-methylphenyl)acetate A mixture of Reference Example 79 (0.5 g), 3,4-methylenedioxybenzyl chloride (0.30 g), potassium carbonate (1.11 g), potassium iodide (130 mg) and tetra-n-butylammonium bromide (20 mg) in methyl ethyl ketone (30 ml) was heated at reflux for 1 hour. The reaction mixture was evaporated and the residue partitioned between water (50 ml) and ethyl acetate (50 ml). The organic phase was separated and the aqueous layer extracted twice with ethyl acetate (50 ml). The combined organic extracts were washed with saturated brine (50 ml), dried over magnesium sulphate and evaporated affording the title compound as a brown oil (0.66 g), which was used without further purification.

REFERENCE EXAMPLE 83

Methyl (RS)-[5-(benzoxazol-5-yl)methoxy-2-cyanophenoxy]-(2-methylphenyl)acetate

A mixture of Reference Example 70 (0.50 g), Reference Example 84 (0.35 g), potassium carbonate (0.23 g), and dimethylformamide (10 ml) was stirred at room temperature for 15 hours. The reaction mixture was concentrated, diluted with water (30 ml), and extracted twice with ethyl acetate (50 ml). The combined extracts were washed twice with 1 N aqueous sodium hydroxide (20 ml), then with brine (20 ml), dried over magnesium sulphate and evaporated. The resulting residue was purified by flash chromatography on silica eluting with a mixture of ethyl acetate and pentane (1:4, v/v). Fractions homogenous in the required product were combined and evaporated to afford the title compound (0.12 g) as a colourless oil.

REFERENCE EXAMPLE 84

5-Bromomethylbenzoxazole

A solution of 5-methylbenzoxazole (0.5 g) in chloroform (20 ml) containing N-bromosuccinimide (0.18 g) and azoisobutyronitrile (0.05 g) was refluxed for 2 hours. After allowing to cool to room temperature the reaction mixture was treated with water (30 ml). The organic phase was separated and the aqueous phase extracted with dichloromethane (30 ml). The combined organic phases were washed with brine (30 ml), dried over magnesium sulphate and evaporated. The residue was triturated with pentane giving the title compound (0.36 g) as an off-white solid, m.p. 90–93° C.

REFERENCE EXAMPLE 85

Methyl (RS)-(5-benzyloxy-2-cyanophenoxy)-(2-methylphenyl)acetate

A mixture of Reference Example 70 (0.50 g), benzyl chloride (0.24 ml), potassium carbonate (0.28 g), and dimethylformamide (10 ml) was stirred at room temperature. After 18 hours the reaction mixture was diluted with water (30 ml) and extracted twice with ethyl acetate (50 ml). The combined organic extracts were washed twice with 1 N aqueous sodium hydroxide (20 ml), then with brine (20 ml), dried over magnesium sulphate and evaporated. The residue was triturated with a mixture of pentane and ethyl acetate giving the title compound (0.49 g) as a white solid, m.p. 134–136° C.

REFERENCE EXAMPLE 86

Methyl (RS)-[2-cyano-5-(furan-3-ylmethoxy)phenoxy]-(2-methylphenyl)acetate

A stirred solution of triphenylphosphine (1.04 g) in tetrahydrofuran (30 ml) was treated with diisopropyl azodicarboxylate (0.78 g) at 0° C. The resulting suspension was stirred for 20 minutes, then treated with a solution of Reference Example 70 (1.19 g) and furan-3-methanol (0.39 g) in tetrahydrofuran (20 ml). After stirring at room temperature for 2 hours the solution was evaporated and the residue dissolved in ether (80 ml). The solution was washed twice with water (20 ml), dried over magnesium sulphate and evaporated. The resulting residue was purified by flash chromatography on silica eluting with a mixture of pentane and ether (3:2, v/v). Fractions homogenous in the required product were combined and evaporated to afford the title compound (1.3 g) as a colourless solid, shown by $^1$HMR to be contaminated with diisopropylhydrazine dicarboxylate.

REFERENCE EXAMPLE 87

α-Bromo-(2-methylphenyl)acetic Acid, (−)-Ephedrine Salt

A solution of (−)-ephedrine (27.17 g) in ethyl acetate (198 ml) was added dropwise over 3 hours to a stirred solution of α-bromo-(2-methylphenyl)acetic acid (39.7 g) and tetra-n-butylammonium bromide (5.75 g) in ethyl acetate (278 ml) keeping the temperature between 20° C. and 23° C. The resulting suspension was stirred at 20–23° C. for 2 hours and filtered. Some of the filtrate (300–350ml) was used to aid transfer of the reaction mixture to the filter. The product was washed twice with ethyl acetate (100 ml), then washed three times with tert-butyl methyl ether (100 ml) and dried at 35–40° C./40–50 torr to give the title compound (47.2 g), ee 78% (for α-bromo-(2-methylphenyl)acetic acid) was determined by chiral HPLC using a Chiralpak AS column (Diacel) and a mobile phase of heptane/isopropanol/trifluoroacetic acid (960/40/2, by volume), with UV detection at 254 nM.

IN VITRO TESTS

A) Preparation of $ET_A$ Receptors

A10 cells are grown to confluence in Dulbecco's modified essential medium containing 10% foetal calf serum. Two days after the final medium change cells are harvested by scraping from the base of the flask and centrifuged at 1500 rpm for 10 minutes at 4° C. in an bench centrifuge. The resulting pellets are washed in 50 mM Hepes buffer pH 7.3 containing calcium chloride (1 mM) and magnesium chloride (5 mM) and resuspended at a density of 140,000 cells/ml in the same. Cell suspensions are then frozen using a mixture of methanol and solid carbon dioxide and stored at −20° C. until required. For use in the assay cells are diluted to the required density with Hepes buffer pH 7.3.

B) Preparation of $ET_B$ Receptors

Rats are killed by cervical dislocation and the cerebellum tissue is removed into ice cold Tris buffer pH 7.4 containing sucrose (0.25 M), ethylenediaminetetracetic acid (3 mM), and a cocktail of protease inhibitors. After homogenizing using a glass/teflon manual homogenizer, the samples are centrifuged at 4° C. for 17 minutes at 1000 g, and the resulting supernatants are retained. This material is centrifuged at 4000 g for 35 minutes at 4° C. and the pellets are resuspended in 50 mM Tris buffer pH 7.4, and the protein concentration is measured. Aliquots of 100 ml are frozen in a mixture of methanol and solid carbon dioxide and stored at −20° C. until required. For use in the assay samples are diluted to the required concentration with Tris buffer pH 7.4 containing 0.1% bovine serum albumin.

C) Assay Methodology

Assays are performed using Millipore 96 well filtration plates with 0.22 μm filters in a final volume of 250 ml. Mixtures consisting of test compound and [$^{125}$I]-ET-1 (20 pM) in buffer pH 7.4 containing 0.1% bovine serum albumin are treated with either A10 cells or cerebellum protein. Total and non-specific binding are measured in the absence and presence of unlabelled ET-1 (100 nM). Approximately 60,000 A10 cells are used per well or 5 μg of cerebellum protein. Plates are incubated for 2 hours at 37° C. before the reaction is terminated by vacuum filtration. Plates are washed twice with assay buffer at 4° C. and the filters are punched out for gamma counting.

D) Results

Compounds within the scope of the invention produce 50% inhibition of the binding of [$^{125}$I]-ET-1 to A10 cell $ET_A$ receptors at concentrations from about $10^{-9}$ M up to about $10^{-6}$ M, preferably from about $10^{-9}$ M up to about $10^{-8}$ M. The compounds of the invention are from about 19,000-fold to about 50-fold more selective for $ET_A$ receptors than $ET_B$ receptors. For example, sodium (S)-[5-(1,3-benzodioxol-5-ylmethoxy)-2-cyanophenoxy]-(2-methylphenyl)acetate produced 50% inhibition of the binding of [$^{125}$I]-ET-1 to A10 cell $ET_A$ receptors at a concentration of 6 nM and 50% inhibition of the binding of [125I]-ET-1 to rat cerebellum $ET_B$ receptors at a concentration of 35000 nM.

IN VIVO TESTS

1) The dose-dependent effect of $ET_A$ antagonists was assessed on the ET-1 mediated pressor response in the presence of BQ 788 in the pithed rat. Male Sprague Dawley rats (250–350 g) were anaesthetised with isoflurane, pithed and artificially respired. The jugular vein and carotid artery were cannulated for administration of vehicle or test compound and measurement of blood pressure and heart rate. BQ 788 (3 mg/kg) and compounds at 25 μmol/kg were given i.v. 10 min prior to ET-1 cumulative dose response curve (0.01–10 nmol/kg). In the pithed rat compounds of this invention caused rightward, parallel dose-dependent shifts from vehicle control. The shift from vehicle for each ET antagonist was calculated using the dose of ET-1 which caused a 40 mm Hg change in diastolic blood pressure. The range in shifts produced by compounds within the scope of this invention at 25 μmol/kg i.v. were from 3 to 80 fold with the preferred activity being closer to 80 fold.

2) Hepatic fibrosis is induced in male Sprague-Dawley rats by one of two methods:

(a) Carbon tetrachloride is administered by the intragastric route at a dose of 0.5 mg/kg once every 5 days for 10 doses (i.e. 50 day insult protocol). Animal weights are monitored as an index of gross toxicity throughout the dosing period and the dose of carbon tetrachloride adjusted accordingly. Compound dosing may be either a prophylactic (commencing 2 days before first carbon tetrachloride dose) or therapeutic regime (commencing 3 days after the first carbon tetrachloride dose). Disease reversal studies are carried out by initiating compound dosing 3 days following the final carbon tetrachloride dose.

(b) Ligation of the bile duct according to the method described by I. Kountouras et al. in Br.J.Exp.Pathol.,65, 301–311(1984).

In both cases compound efficacy is assessed by histomorphometry of collagen deposition in the tissue.

3) Myocardial fibrosis is studied in hamsters genetically susceptible to cardiomyopathy and show a strong, progressive, deposition of collagen in the ventricular wall (Gertz, Prog.Exp.Tumour Res.,16,242–260(1972)). This lesion is accurately quantified by histomorphometry of collagen deposition in the tissue. Compounds are dosed during lesion development (typically 1–3 months) or after lesion maturation (typically 6 months).

4) Renal fibrosis (sclerosis) is induced by surgical occlusion of the renal blood supply initiating a focal ischaemia leading to fibrosis. Compound administration in this model addresses disease reversal.

What is claimed is:

1. A compound of formula I:

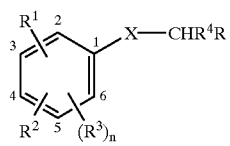

(I)

wherein
$R^1$ is CN, $CH_2CN$, CH=CHCN, CHO, or CH=CHCO$_2$H;
$R^2$ is heteroaryl lower alkoxy or heteroaryl lower alkylthio wherein each of the heteroaryl moieties is optionally substituted;
$R^3$ is halogen;
$R^4$ is optionally substituted alyl or optionally substituted heteroaryl;
$R^5$ is caboxy, sulpho, phosphono, alkylsulphonylcarbamoyl, tetrazolyl, arylsulphonylcarbamoyl, heteroarylsulphonylcarbamoyl or N-methoxycarbamoyl;
X is oxygen or sulphur; and
n is zero or 1;
and wherein said heteroaryl is a thienyl ring; or an N-oxide thereof, solvate thereof or pharmaceutically acceptable salt thereof.

2. The compound according to claim 1 wherein $R^1$ is attached at the ring 2-position.

3. The compound according to claim 1 wherein $R^1$ is CN.

4. The compound according to claim 1 wherein $R^2$ is attached at the ring 5-position.

5. The compound according to claim 1 wherein $R^2$ is thienyl lower alkoxy.

6. The compound according to claim 5 wherein $R^2$ is thienylmethoxy.

7. The compound according to claim 1 wherein $R^3$ is attached at the ring 3-position.

8. The compound according to claim 1 wherein $R^3$ is a fluorine atom.

9. The compound according to claim 1 wherein $R^4$ is optionally substituted aryl.

10. The compound according to claim 1 wherein $R^4$ is phenyl substituted in the ortho position relative to the attachment of the phenyl group to the rest of the $R^4$ moiety by lower alkyl, $CF_3$ or chlorine and is optionally further substituted by one or more of halogen, lower alkyl, CN or lower alkoxy.

11. The compound according to claim 1 claim wherein $R^5$ is carboxy.

12. The compound according to claim 1 wherein X is oxygen.

13. The compound according to claim 1 wherein the chiral center associated with the carbon atom α to the moiety X within the group —X—CHR$^4$R$^5$ has the (S) configuration.

14. A compound of formula Ia:

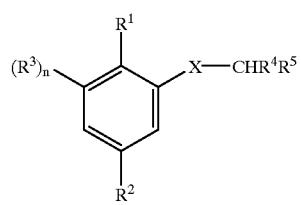

(Ia)

wherein $R^1$, $R^2$, $R^3$, $R^4$, $R^5$, n and X are as defined in claim 1, on an N-oxide thereof, solvate thereof or pharmaceutically acceptable salt thereof.

15. A compound of formula Ib:

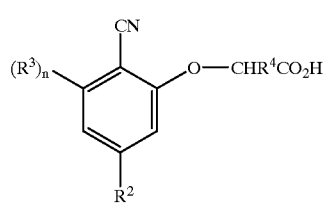

(Ib)

wherein $R^2$, $R^3$, $R^4$, and n are as defined in claim 1, on an N-oxide thereof, solvate thereof or pharmaceutically acceptable salt thereof.

16. A compound selected from the group consisting of:
(RS)-[2-cyano-5-(3-thienylmethoxy)phenoxy]-phenylacetic acid;
(RS)-(2-chlorophenyl)-[2-cyano-5-(3-thienylmethoxy)phenoxy]acetic acid;
(RS)-[2-cyano-5-(3-thenylmethox)phenoxy]-(2-methylphenyl)acetic acid;
(RS)-(2-bromophenyl)-[2-cyano-5-(3-thienylmethoxy)phenoxy]acetic acid;

(RS)-(3-chlorophenyl)-(2-cyano-5-(3-thienylmethoxy)-phenoxy]acetic acid;
(R)-(2-chlorophenyl)-[2-cyano-5-(3-thienylmethoxy)-phenoxy]acetic acid;
(S)-(2-chlorophenyl)-[2-cyano-5-(3-thienylmethoxy)-phenoxy]acetic acid;
(RS)-[2-cyano-5-(3-thienylmethoxy)phenoxy]-(2-fluorophenyl)acetic acid;
(RS)-[2-cyano-5-(3-thienylmethoxy)phenoxy]-(2-trifluoromethylphenyl)acetic acid;
(RS)-[2-formyl-5-(3-thienylmethoxy)phenoxy]phenylacetic acid;
(RS)-N-{[2-cyano-5-(3-thienylmethoxy)phenoxy]-phenylacetyl}-4-isopropylbenzenesulphonamide;
(RS)-(2-chlorophenyl)-[2-cyano-3-fluoro-5-(3-thienylmethoxy)phenoxy]acetic acid; and
(RS)-N-methoxy-[2-cyano-5-(3-thienylmethoxy)phenoxy]-(2-methylphenyl)acetamide, or a solvate thereof or a pharmaceutically acceptable salt thereof.

17. A pharmaceutical composition comprising a pharmaceutically acceptable amount of the compound according to claim 1 and a pharmaceutically acceptable carrier or excipient.

18. A method of treating a patient subject to a disease state associated with a physiological detrimental excess of endothelin or a disease state associated with a pathological condition that is modulated by inhibiting endothelin comprising administering to said patient a pharmaceutically effective amount of the compound according to claim 1.

19. The method according to claim 18 further comprising administering a pharmaceutically effective amount of an endothelin converting enzyme inhibitor, angiotensin II receptor antagonist, renin inhibitor, angiotensin converting enzyme inhibitor, α- and β-adrenoceptor agonist or antagonist, diuretic, potassium channel activator, calcium channel antagonist, nitrate, antiarrhythmic agent, positive inotropic agent, serotonin receptor agonist or antagonist, platelet activating factor antagonist, histamine receptor antagonist, proton pump inhibitor, antithrombotic and thrombolytic agent, lipid lowering agent, antibiotic agent, or phosphodiesterase inhibitor.

* * * * *

UNITED STATES PATENT AND TRADEMARK OFFICE
CERTIFICATE OF CORRECTION

PATENT NO. : 6,124,343
DATED : September 26, 2000
INVENTOR(S) : C. Smith et al.

It is certified that error appears in the above-identified patent and that said Letters Patent is hereby corrected as shown below:

Title page,
Item [30], Foreign Application Priority Data, replace "Jan. 27, 1919", with
-- Jan. 27, 1995 --.

Column 59,
Lines 40-48, replace " 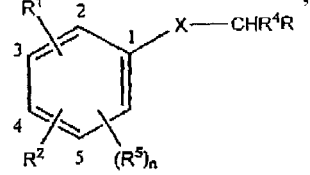 " with -- 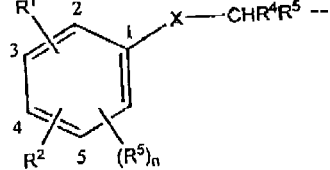 --.

Signed and Sealed this

Sixteenth Day of May, 2006

JON W. DUDAS
*Director of the United States Patent and Trademark Office*